US011613782B2

(12) United States Patent
Suliman et al.

(10) Patent No.: US 11,613,782 B2
(45) Date of Patent: Mar. 28, 2023

(54) METHOD FOR PREDICTING PROGRESSION TO ACTIVE TUBERCULOSIS DISEASE

(71) Applicants: UNIVERSITY OF CAPE TOWN, Cape Town (ZA); STELLENBOSCH UNIVERSITY, Cape Town (ZA); SEATTLE CHILDREN'S HOSPITAL, Seattle, WA (US); MAX-PLANCK-GESELLSCHAFT ZUR FOERDERUNG DER WISSENSCHAFTEN E.V, Munich (DE); UNITED KINGDOM RESEARCH AND INNOVATION, Swindon (GB)

(72) Inventors: Sara Suliman, Brookline, MA (US); Ethan Greene Thompson, Seattle, WA (US); Jayne Suzanne Sutherland, Banjul (GM); Stefan H. E. Kaufmann, Berlin (DE); Thomas Jens Scriba, Cape Town (ZA); Daniel Edward Zak, Seattle, WA (US); Gerhard Walzl, Cape Town (ZA)

(73) Assignees: UNIVERSITY OF CAPE TOWN, Cape Town (ZA); STELLENBOSCH UNIVERSITY, Cape Town (ZA); SEATTLE CHILDREN'S HOSPITAL, Seattle, WA (US); MAX-PLANCK-GESELLSCHAFT ZUR FOERDERUNG DER WISSENSCHAFTEN E.V, Munich (DE); UNITED KINGDOM RESEARCH AND INNOVATION, Swindon (GB)

( * ) Notice: Subject to any disclaimer, the term of this patent is extended or adjusted under 35 U.S.C. 154(b) by 0 days.

(21) Appl. No.: 16/980,121

(22) PCT Filed: Mar. 13, 2019

(86) PCT No.: PCT/IB2019/052043
§ 371 (c)(1),
(2) Date: Sep. 11, 2020

(87) PCT Pub. No.: WO2019/175803
PCT Pub. Date: Sep. 19, 2019

(65) Prior Publication Data
US 2021/0363580 A1 Nov. 25, 2021

(30) Foreign Application Priority Data
Mar. 13, 2018 (GB) ...................... 1804019

(51) Int. Cl.
C12Q 1/68 (2018.01)
C12P 19/34 (2006.01)
C12Q 1/6883 (2018.01)

(52) U.S. Cl.
CPC ...... *C12Q 1/6883* (2013.01); *C12Q 2600/106* (2013.01); *C12Q 2600/118* (2013.01); *C12Q 2600/158* (2013.01)

(58) Field of Classification Search
CPC ............ C12Q 1/6883; C12Q 2600/106; C12Q 2600/118; C12Q 2600/158; C12Q 2537/165
See application file for complete search history.

(56) References Cited

FOREIGN PATENT DOCUMENTS

| GB | 2547034 | 8/2017 |
|----|---------|--------|
| WO | 2011/066008 | 6/2011 |
| WO | 2017/081618 | 7/2017 |

OTHER PUBLICATIONS

Jacqueline M. Cliff, et al. "Distinct Phases of Blood Gene Expression Pattern Through Tuberculosis Treatment Reflect Modulation of the Humoral Immune Response". The Journal of Infectious Diseases, vol. 207, Issue 1, Jan. 1, 2013, pp. 18-29 (Year: 2013).*
Timothy E Sweeney, et al. "Genome-wide expression for diagnosis of pulmonary tuberculosis: a multicohort analysis" Lancet Respir Med. Mar. 2016 ; 4(3): 213-224. (Year: 2016).*
Chen, Guoan, et al. "Discordant protein and mRN A expression in lung adenocarcinomas." Molecular & cellular proteomics 1.4 (2002): 304-313. (Year: 2002).*
Cheung, Vivian G., et al. "Natural variation in human gene expression assessed in lymphoblastoid cells." Nature genetics 33.3 (2003): 422-425. (Year: 2003).*
Cobb, J. Perren, et al. "Sepsis gene expression profiling: murine splenic compared with hepatic responses determined by using complementary DNA microarrays." Critical care medicine 30.12 (2002): 2711-2721. (Year: 2002).*
Hoshikawa, Yasushi, et al. "Hypoxia induces different genes in the lungs of rats compared with mice." Physiological genomics 12.3 (2003): 209-219. (Year: 2003).*
International Search Report and Written Opinion corresponding to International Patent Application No. PCT/IB2019/052043, dated Jun. 4, 2019, 12 pages.

(Continued)

Primary Examiner — Stephen T Kapushoc
(74) Attorney, Agent, or Firm — Myers Bigel, P.A.

(57) ABSTRACT

The invention provides a gene signature for use in determining a likelihood of a latent tuberculosis (TB) infection in a subject transitioning to active TB disease. The gene signature comprises at least SEPT4 and BLK, and optionally also GAS6 and/or CD1C. Expression levels of these genes are detected in a sample from the subject, and the ratios of expression of at least two of the above genes are calculated (e.g. SEPT4:BLK, SEPT4:CD1C, GAS6:BLK and/or GAS6:CD1C). A score is assigned to each ratio, the score being indicative of the likelihood of the latent TB infection transitioning into active TB disease, based on the ratio for the respective gene pair. The subject can be identified as having a latent TB infection that is likely to transition into active TB disease or that is not likely to transition into active TB disease based on the score or on the average of the scores.

3 Claims, 7 Drawing Sheets

(56) References Cited

OTHER PUBLICATIONS

Suliman et al. "Four-Gene Pan-African Blood Signature Predicts Progression to Tuberculosis" American Journal of Respiratory and Critical Care Medicine, 197(9):1198-1208 2018.
Maertzdorf, Jeroen, et al., "Concise gene signature for point-of-care classification of tuberculosis", EMBO Molecular Medicine. 8(2):86-95 (2016).
Sweeney, Timothy E., et al., "Genome-wide expression for diagnosis of pulmonary tuberculosis: a multicohort analysis" Lancet Respir Med. 4(3):213-224 (2016).
Thompson, Ethan G., et al., "Host blood RNA signatures predict the outcome of tuberculosis treatment" Tuberculosis.107:48-58 (2017).
Zak, Daniel E., "A prospective blood RNA signature for tuberculosis disease risk" Lancet. 387:2312-2322 (2016).

\* cited by examiner

Fig 4
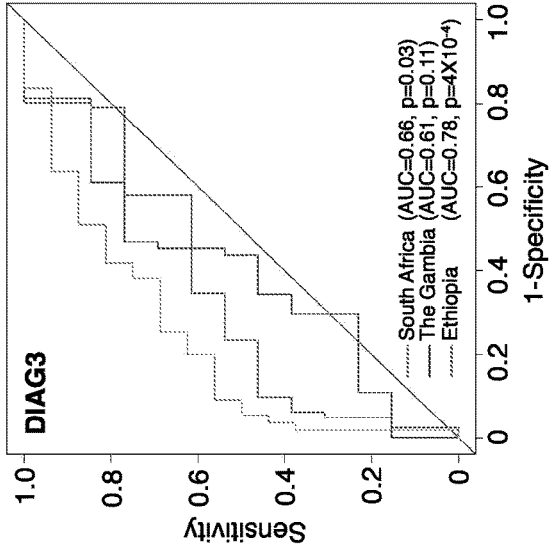
A) PCR-adapted signatures
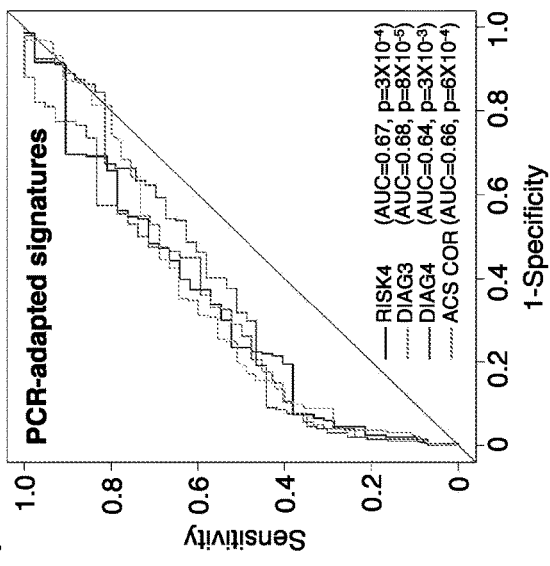
C) DIAG4
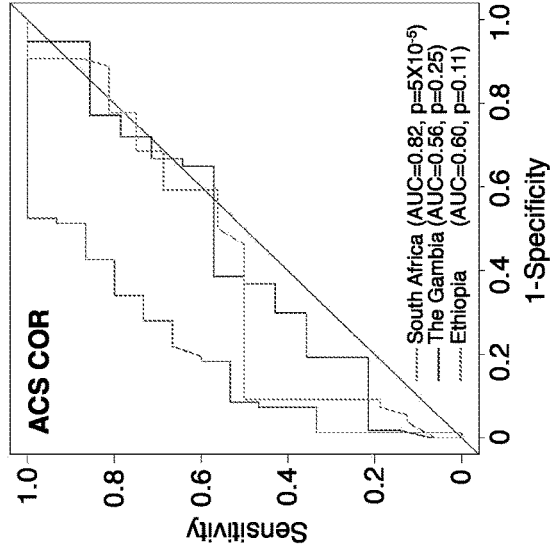
B) DIAG3
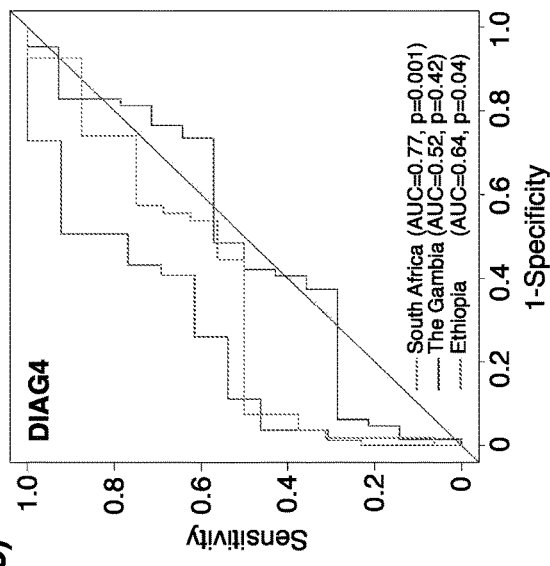
D) ACS COR

Fig 7
A)
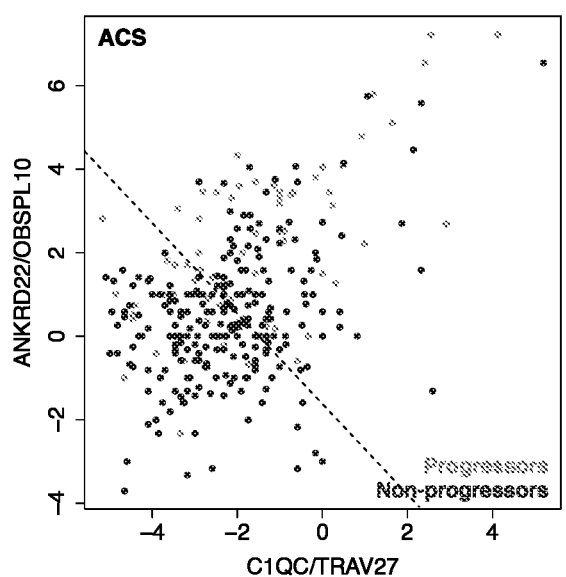
B)
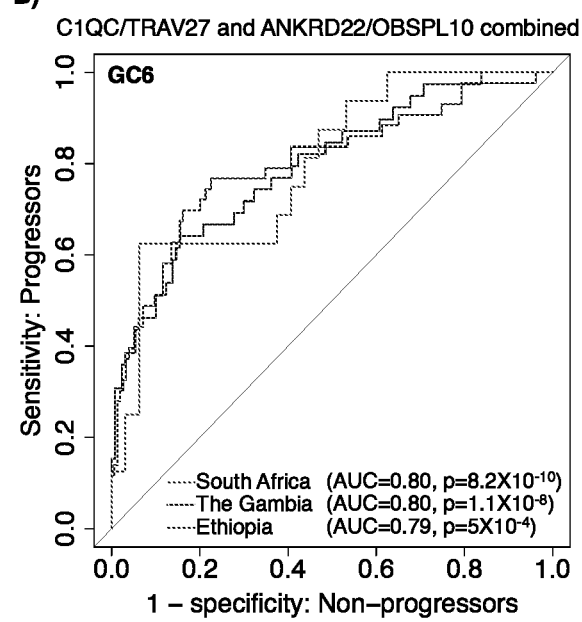

METHOD FOR PREDICTING PROGRESSION TO ACTIVE TUBERCULOSIS DISEASE

STATEMENT REGARDING SPONSORED RESEARCH OR DEVELOPMENT

This invention was made with funding by Bill & Melinda Gates Foundation grants OPP1065330, OPP1023483 and OPP1055806 and GC6-74 Grant no. 37772, and grants from the National Institutes of Health (NIH) grants: R01AI087915, U01AI115619 and NO1AI095383/AI070022. The study was also supported by the Strategic Health Innovation Partnerships (SHIP) Unit of the South African Medical Research Council with funds received from the South African Department of Science and Technology. Individual researchers were also supported by The Carnegie Corporation of New York, the South African National Research Foundation, The Claude Leon Foundation, the Columbia University-Southern African Fogarty AIDS International Training and Research Program (AITRP) through the Fogarty International Center, NIH (D43 TW000231) and EC HORIZON2020 TBVAC2020 (Grant Agreement No. 643381).

CROSS-REFERENCE TO RELATED APPLICATIONS

This application claims priority from United Kingdom patent application number 1804019.6 filed on 13 Mar. 2018.

FIELD OF THE INVENTION

The invention relates generally to a method of determining a likelihood of a subject, who has been exposed to a patient with active pulmonary TB, progressing to active TB disease. In particular, the invention relates to gene biomarkers that can be used to detect whether a subject is likely to develop active TB.

BACKGROUND OF THE INVENTION

Tuberculosis (TB), caused by infection with *Mycobacterium tuberculosis* (M.tb), is the leading cause of death caused by a single pathogen globally. TB exists in a dynamic spectrum from latent infection to symptomatic disease, and intervention requires a multi-pronged approach including treatment and prevention. Most infected individuals have effective defense mechanisms to control M.tb and only 5-10% will progress to TB during their lifetime. Despite this, over 10 million new cases of TB are diagnosed each year and almost 2 million people die from the disease. Prior to development of disease, latent M.tb infection can be detected by measuring immunological sensitization, using the tuberculin skin test (TST) and/or interferon gamma release assays (IGRA). Although recent M.tb exposure and TST or IGRA conversion are associated with higher risk of TB progression, the positive predictive values of these tests are low, i.e. 1.5% and 2.7%, falling short of current WHO supported guidelines. With 1.7 billion people globally estimated to be infected with M.tb, the number of TST or IGRA-positive individuals requiring treatment to prevent progression to a single incident case of TB is thus prohibitively high.

Factors associated with elevated risk of progression to TB include age, sex, comorbidities, and especially being in recent contact with a patient with active pulmonary TB. A biomarker that identifies people who have been in recent contact with a patient with active pulmonary TB (referred to as "household contacts" or "HHC") who will progress to TB would provide an opportunity to arrest disease progression through targeted prophylactic intervention. Such prognostic biomarkers would be most impactful as point-of-care tests for resource-limited settings, such as those in Sub-Saharan Africa. Test performance should not be adversely affected by geographical diversity, as seen in Africa, which has a diversity of ethnic backgrounds and circulating M.tb lineages. A 'TB-risk' test must be practical for field application and therefore based on accessible biological samples routinely used in clinical settings, such as peripheral blood.

A 16-gene blood transcriptional correlate of risk (COR) signature that predicts risk of progression to TB in M.tb-infected HIV-negative South African adolescents and HHC from South Africa and The Gambia has previously been identified[1]. However, given that this COR signature was developed using a single cohort of latently M.tb-infected South African adolescents without a known exposure event, the predictive accuracy for HHC in diverse African populations may be sub-optimal. It would also be desirable to reduce the number of transcripts in the signature, to facilitate implementation of a low-cost point-of-care test.

Consequently, there is still a need for a method of identifying asymptomatic individuals who are at high risk of progressing to TB, so as to help prioritize preventative strategies and lead to better TB control.

SUMMARY OF THE INVENTION

According to a first embodiment of the invention, there is provided a method of determining a likelihood of a latent tuberculosis (TB) infection in a subject transitioning to active TB disease, the method comprising the steps of:
a) detecting gene expression levels of SEPT4 and BLK, and optionally also one or both of GAS6 and CD1C, in a biological sample from the subject;
b) calculating the ratios of expression for SEPT4:BLK and optionally also ratios of expression for SEPT4:CD1C, GAS6:BLK and/or GAS6:CD1C; and
c) identifying the subject as having a latent TB infection that is likely to transition into active TB disease or that is not likely to transition into active TB disease based on the ratio(s) of expression.

The gene expression levels of SEPT4 and BLK may be detected, and the ratio of expression of SEPT4:BLK may be calculated. Alternatively, the gene expression levels of SEPT4, BLK and GAS6 may be detected, and the ratios of expression of SEPT4:BLK and GAS6:BLK may be calculated. Alternatively, the gene expression levels of SEPT4, BLK and CD1C may be detected, and the ratios of expression of SEPT4:BLK and SEPT4:CD1C may be calculated. Alternatively, the gene expression levels of SEPT4, BLK, GAS6 and CD1C may be detected, and the ratios of expression of SEPT4:BLK, SEPT4:CD1C, GAS6:BLK and GAS6:CD1C may be calculated.

The ratio(s) of expression may be compared with respective reference ratios of expression for SEPT4:BLK, SEPT4:CD1C, GAS6:BLK and/or GAS6:CD1C, or with values relating thereto.

A score may be assigned to each ratio, the score being indicative of the likelihood of the latent TB infection transitioning into active TB disease, based on the ratio for the respective gene pair. The subject may be identified as having a latent TB infection that is likely to transition into active TB disease or that is not likely to transition into active TB disease based on the average of the scores.

The subject may be identified as having a latent TB infection that is likely to transition into active TB disease if the ratio of any one or more of the gene pairs is above a reference threshold value for the respective gene pair(s).

The reference threshold value or score for each gene pair may be derived from gene expression ratios of the respective gene pairs in samples from a training cohort in which subjects were subsequently identified as having progressed to active TB or not having progressed to active TB within a given period of time from each sample having been obtained from the subjects.

The subject may be identified as being likely to transition to active TB disease within a period of 2 years.

The gene transcript levels may be detected by qRT-PCR or other means of measuring gene expression levels.

The sample may be a blood sample.

According to a second embodiment of the invention, there is provided a method of diagnosing and treating tuberculosis (TB) infection in a subject, the method comprising the steps of:
a) detecting gene expression levels of SEPT4 and BLK, and optionally also one or both of GAS6 and CD1C, in a biological sample from the subject;
b) calculating the ratios of expression for SEPT4:BLK and optionally also ratios of expression for SEPT4:CD1C, GAS6:BLK and/or GAS6:CD1C;
c) identifying the likelihood of the subject having a latent TB infection that will transition into active TB disease or that won't transition into active TB disease based on the ratio(s) of expression; and
d) administering treatment for tuberculosis infection to the subject if the subject is identified as having a latent TB infection that is likely to transition into active TB disease.

The treatment may be prophylactic treatment.

According to a third embodiment of the invention, there is provided a method of determining whether treatment for tuberculosis (TB) infection should be administered to a subject who does not have symptoms of active TB disease, the method comprising the steps of:
a) detecting gene expression levels of SEPT4 and BLK, and optionally also one or both of GAS6 and CD1C, in a biological sample from the subject;
b) calculating the ratios of expression for SEPT4:BLK and optionally also ratios of expression for SEPT4:CD1C, GAS6:BLK and/or GAS6:CD1C;
c) identifying the likelihood of the subject having a latent TB infection that will transition into active TB disease or that won't transition into active TB disease based on the ratio(s) of expression; and
d) administering treatment for TB infection to the subject if the subject is identified as having a latent TB infection that is likely to transition into active TB disease.

The treatment may be prophylactic treatment.

According to a fourth embodiment of the invention, there is provided a kit comprising primer-probes for measuring levels of expression of SEPT4 and BLK genes, and optionally also one or both of GAS6 and CD1C genes, in a sample from a subject.

The primer-probes may be NM_000820_10_11 and Hs01017452_m1, and optionally also one or both of Hs00910208_g1 and Hs00957534_g1.

The kit may further comprise information, in electronic or paper form, comprising instructions to calculate the expression ratio(s) of SEPT4:BLK, SEPT4:CD1C, GAS6:BLK and/or GAS6:CD1C and to correlate the expression ratio of each gene pair with the likelihood of the subject developing active tuberculosis.

According to a fifth embodiment of the invention, there is provided a computer implemented method for identifying whether a subject having a latent TB infection is likely to transition into active TB disease, the computer performing steps comprising:
a) receiving inputted subject data comprising values for levels of expression of SEPT4 and BLK genes, and optionally also one or both of GAS6 and CD1C genes, in a biological sample from the subject;
b) calculating a ratio of the transcript levels of SEPT4:BLK and optionally also ratios of the transcript levels of SEPT4:CD1C, GAS6:BLK and/or GAS6:CD1C;
c) determining likelihood of the subject transitioning into active TB disease based on the ratio(s) of expression; and
d) displaying information regarding the prognosis of the subject.

According to a sixth embodiment of the invention, there is provided a method of determining a likelihood of a latent tuberculosis (TB) infection in a subject transitioning to active TB disease, the method comprising the steps of:
a) detecting gene expression levels of C1QC and TRAV27 in a biological sample from the subject;
b) calculating the ratio of expression for C1QC:TRAV27; and
c) identifying the likelihood of the subject having a latent TB infection that will transition into active TB disease or that won't transition into active TB disease based on the ratio of expression of C1QC:TRAV27.

According to a seventh embodiment of the invention, there is provided a method of determining a likelihood of a latent tuberculosis (TB) infection in a subject transitioning to active TB disease, the method comprising the steps of:
d) detecting gene expression levels of ANKRD22 and OSBPL10 in a biological sample from the subject;
e) calculating the ratio of expression for ANKRD22:OSBPL10; and
f) identifying the subject as having a latent TB infection that is likely to transition into active TB disease or that is not likely to transition into active TB disease based on the ratio of expression of ANKRD22:OSBPL10.

BRIEF DESCRIPTION OF THE FIGURES

FIG. 4: Comparison of RISK4 and published small TB diagnostic signatures. (A) ROC curves for blind predictions of RISK4 (Black: AUC=0.67 [0.57-0.77], p=$2.6 \times 10^{-4}$), DIAG3 (red: AUC=0.68 [0.59-0.78], p=$8.4 \times 10^{-5}$), DIAG4 (blue: AUC=0.64 [0.53-0.74], p=$2.6 \times 10^{-3}$) and ACS COR (green: AUC=0.66 [0.55-0.76], p=$5.8 \times 10^{-4}$) in all test set samples. (B-D) Blind prediction of published small signatures: DIAG3 (B: South Africa AUC=0.66 [0.47-0.84], The Gambia AUC=0.6 [0.45-0.77] and Ethiopia AUC=0.78 [0.64-0.92]), DIAG4 (C: South Africa AUC=0.77 [0.62-0.91], The Gambia AUC=0.52 [0.33-0.71] and Ethiopia AUC=0.64 [0.46-0.83]) and RISK16 (D: South Africa AUC=0.82 [0.71-0.92], The Gambia AUC=0.56 [0.37-0.75] and Ethiopia AUC=0.6 [0.41-0.79]). South Africa, The Gambia and Ethiopia AUCs are depicted in red, blue and green, respectively.

FIG. 7: Complementation of pair ratios of C1QC/TRAV27 with ANKRD22/OBSPL10. Scatterplot of C1QC/TRAV27 complementation with the top pair ANKRD22/OBSPL10 on the natural history cohort of South African latently M.tb-infected adolescents (Adolescents Cohort Study: ACS; Zak, et al. Lancet 2016). S2B: Area under the Receiver Operators Characteristics Curve corresponding to the linear combination of C1QC/TRAV27 and ANKRD22/OBSPL10 on each of the three African household contact cohorts separately: South Africa (red) with AUC=0.81 [0.72-0.88], p=8.16×10-10; The Gambia (blue) with AUC=0.8 [0.71-0.88], p=1.13×10-8; and Ethiopia (green) with AUC=0.79 [0.66-0.93], p=5×10-4.

DETAILED DESCRIPTION OF THE INVENTION

Figure 1:
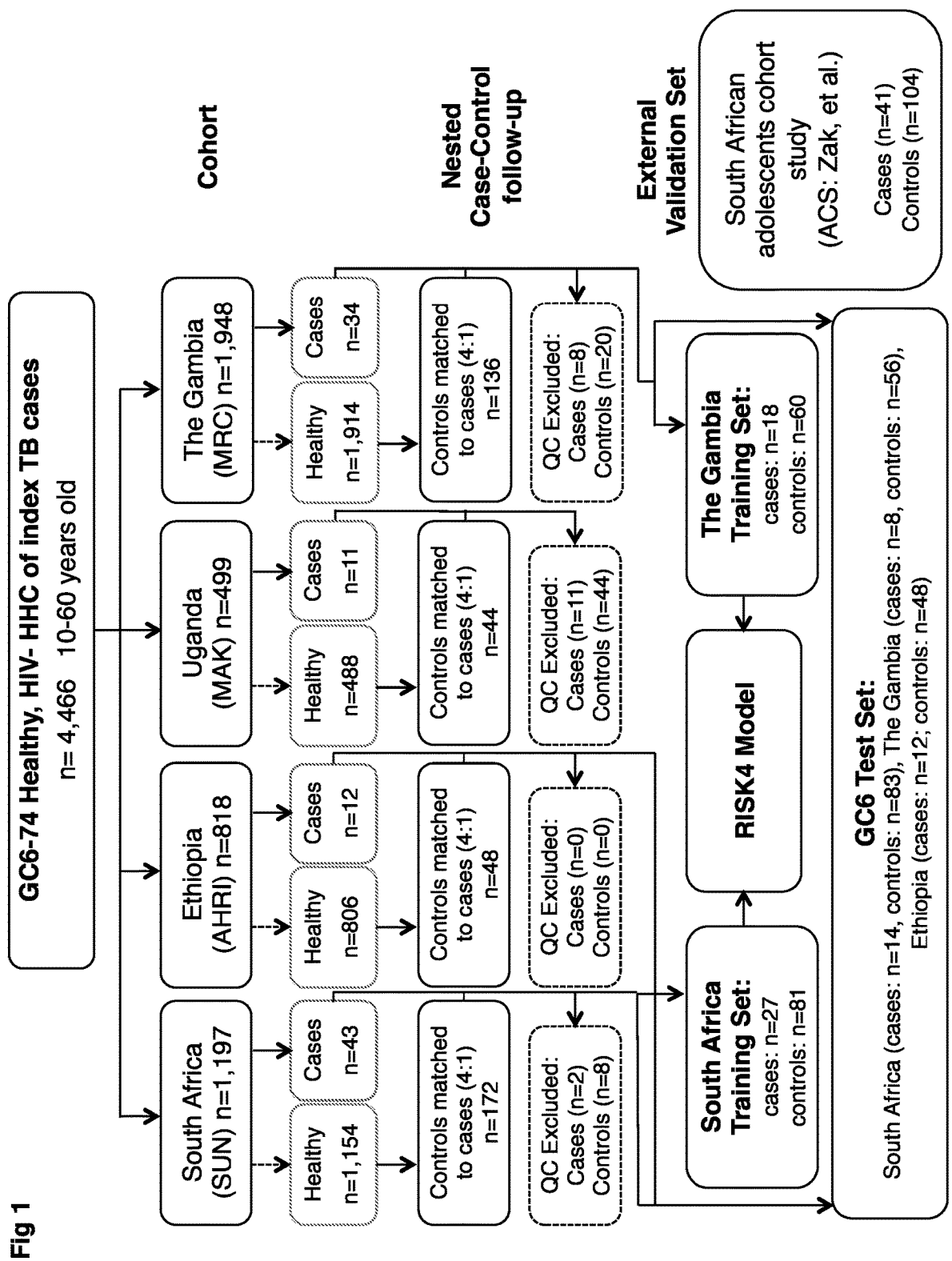
FIG. 1: Consort diagram describing the inclusion and exclusion of participants from different African cohorts. Stellenbosch University in South Africa (SUN), Armauer Hansen Research Institute in Ethiopia (AHRI), Makerere University in Uganda (MAK), Medical Research Council in The Gambia (MRC), and the external validation natural history study of South African Adolescents (ACS) in training predictive transcriptomic biomarker for TB progression.

The invention provides a gene signature for use in determining a likelihood of a latent tuberculosis (TB) infection in a subject transitioning to active TB disease. The gene signature comprises at least SEPT4 and BLK, and optionally also GAS6 and/or CD1C. The signature is based on the findings, described below, that the expression levels of SEPT4 and GAS6 are increased and the expression levels of BLK and CD1C are decreased in subjects who have been exposed to *Mycobacterium tuberculosis* and are likely to develop active TB disease. Expression levels of these genes can be detected in a biological sample from a subject, and based on the ratios of expression of at least two of the above genes, the likelihood of whether the subject will develop active TB or not can be determined.

In one embodiment of the invention, gene expression levels of SEPT4 and BLK are detected, and the ratio of expression of SEPT4:BLK is calculated. In an alternative embodiment, the gene expression levels of SEPT4, BLK and GAS6 are detected, and the ratios of expression of SEPT4:BLK and GAS6:BLK are calculated. In an alternative embodiment, the gene expression levels of SEPT4, BLK and CD1C are detected, and the ratios of expression of SEPT4:BLK and SEPT4:CD1C are calculated. In an alternative embodiment, the gene expression levels of SEPT4, BLK, GAS6 and CD1C are detected, and the ratios of expression of SEPT4:BLK, SEPT4:CD1C, GAS6:BLK and GAS6:CD1C are calculated.

A score (or value) can be assigned to each ratio, the score being indicative of the likelihood of the latent TB infection transitioning into active TB disease, based on the ratio for the respective gene pair. This information can be presented in a look-up table or computer program. The subject can be identified as having a latent TB infection that is likely to transition into active TB disease or that is not likely to transition into active TB disease based on the average of the scores.

In one embodiment, the subject can be identified as having a latent TB infection that is likely to transition into active TB disease if the ratio of any one or more of the gene pairs is above a reference threshold value (or cut-off value) for the respective gene pair(s).

The reference threshold value or score for each gene pair can be derived from gene expression ratios of the respective gene pairs in samples from a training cohort in which subjects were subsequently identified as having progressed to active TB or not having progressed to active TB within a given period of time from each sample having been obtained from the subjects.

The sample can be a blood sample, such as whole blood or fractionated blood (e.g. leukocytes, peripheral blood mononuclear cells, buffy coat, plasma or serum).

In one embodiment of the invention, the expression levels of the genes in the signature are detected by measuring mRNA in the sample from the subject. One method for doing this is to measure mRNA expression levels by reverse transcription quantitative polymerase chain reaction (qRT-PCR). This and other methods of measuring expression levels of mRNA are known in the art and are described in detail in, for example: "Gene Expression Profiling: Methods and Protocols" by Richard A. Shimkets, editor, Humana Press, 2004; www.qiagen.com/resources/molecular-biology-methods/; "Methods in Molecular Biology", Ed. J. M. Walker, Humana Press, ISSN: 1064-3745; "Molecular Cloning: A Laboratory Manual" by Michael R Green and Joseph Sambrook 2012, Cold Spring Harbour Laboratory Press, ISBN: 978-1-9361 13-42-2.

In one embodiment of the invention, the primer-probes used to detect the gene expression levels are those listed in Table 1.

TABLE 1

Primer-probes for GAS6, SEPT4, CD1C and BLK genes, and pairwise structure for calculating risk of TB progression

| Pair number | Primer-probe ID #1 | Primer-probe ID #2 |
| --- | --- | --- |
| 1 | GAS6_NM_000820_10_11 | CD1C_Hs00957534_g1 |
| 2 | SEPT4_Hs00910208_g1 | BLK_Hs01017452_m1 |
| 3 | SEPT4_Hs00910208_g1 | CD1C_Hs00957534_g1 |
| 4 | GAS6_NM_000820_10_11 | BLK_Hs01017452_m1 |

(available from Applied Biosystems TaqMan Assays)

The likelihood of the subject transitioning to active TB disease may be for a particular period from the time of obtaining the sample, e.g. within 2 years.

If the subject is identified as being likely to transition into active TB, then treatment for tuberculosis infection can be prescribed for, and administered to, the subject. The treatment may be prophylactic or preventative treatment. Alternatively, the subject can be regularly monitored for signs of active TB.

A kit that includes primer-probes for detecting gene expression levels of the above-mentioned genes can be provided. Suitable primer-probes include NM_000820_10_11, Hs01017452_m1, Hs00910208_g1 and Hs00957534_g1, but a person skilled in the art will understand that other probes could also be used.

The kit can further include information, in electronic or paper form, with instructions to calculate the expression ratio(s) of the gene pairs described above and to correlate the expression ratio of each gene pair with the likelihood of the subject developing active tuberculosis.

A computer implemented method for identifying whether a subject having a latent TB infection is likely to transition into active TB disease is also provided, so that the computer performs the steps of:

a) receiving inputted subject data comprising values for levels of expression of the genes in the gene signature in a biological sample from the subject;

b) calculating ratio(s) of the transcript levels of the gene pairs described above;

c) determining whether the subject is likely to transition into active TB disease based on the ratio(s) of expression; and d) displaying information regarding the prognosis of the subject.

"Tuberculosis infection" or "TB infection" refers to *Mycobacterium tuberculosis* infection of an individual. TB infection encompasses both "latent TB infection" (non-transmissible and without disease symptoms) and "active TB infection" (transmissible and symptomatic). Observable signs of active TB infection include, but are not limited to, chronic cough with blood-tinged sputum, fever, night sweats, and weight loss. A clinical diagnosis of Active TB is typically made on the basis of a positive microbiology laboratory test using sputum or another respiratory specimen that confirms detection of acid-fast bacilli, including XpertTB-RIF®, smear microscopy or sputum culture test.

As used in this application, the singular forms "a," "an," and "the" include the plural, unless the context clearly dictates otherwise, and may be used interchangeably with "at least one" and "one or more."

The terms "comprises," "comprising," "includes," "including," "contains," "containing" and any variations thereof are intended to cover a non-exclusive inclusion, such that a process, method, product-by-process, or composition of matter that comprises, includes, or contains an element or list of elements may include other elements not expressly listed.

As used herein, "individual" and "subject" and "patient" are used interchangeably to refer to a test subject or patient.

The term "gene" refers to a unit of inheritance, including the protein coding and noncoding transcribed regions, upstream and downstream regulatory regions, transcribed regions, and all variants of the mature transcript, including microRNAs.

The terms "RNA" and "RNA transcript" are used interchangeably and mean an RNA molecule transcribed from the DNA of a gene.

The term "progressor" means an asymptomatic, otherwise healthy individual who does not have definite or suspected TB disease, despite other possible infections or diseases, who developed definite TB disease during follow-up in either the ACS or GC6 studies.

"Prognostic" means an indication of infection in an otherwise healthy individual before the onset of the TB disease symptoms which would typically trigger health seeking behavior and subsequent diagnosis.

The phrase "splice junction" means the nucleic acid sequence in a mature mRNA that results from the joining of two exons encoded by the same gene. "Pairs of mRNA splice junctions" means a set of discrete splice junctions encoded by different genes.

The molecular techniques referenced herein, including RNA extraction and purification, RNA sequencing, amplification, primer and oligonucleotide probe design, microarray printing and methods, and qRT-PCR are all standard methods known to those skilled in the art. Many reference sources are available, including but not limited to: www.qiagen.com/resources/molecular-biology-methods/; "Methods in Molecular Biology", Ed. J. M. Walker, Humana Press, ISSN: 1064-3745; and "Molecular Cloning: A Laboratory Manual" by Michael R Green and Joseph Sambrook 2012, Cold Spring Harbour Laboratory Press, ISBN: 978-1-9361 13-42-2.

The Pair Ratio approach[3] can be used to calculate whether the qRT-PCR measurements of the gene transcript levels are indicative of the subject developing active TB. In this approach, the relative abundance of two genes which are regulated in opposite directions during TB progression are directly compared. Thus, ratios of expression for the following predictive gene pairs are calculated: SEPT4/BLK and optionally also SEPT 4/CD1C, GAS6/BLK and/or GAS6/CD1C (Table 1).

Each transcript expression ratio is converted into a score. This can be done by referring to a look-up table for each gene pair, which may be in printed or electronic form. The look-up table lists various expression ratios and provides a score (typically between 0 and 1) for each of the listed ratios, the score having been calculated by comparing the ratio to the distribution of ratios present in a training set. The ratio is compared to all ratios from TB progressors and controls in training cohorts. The score for a particular sample is computed as the average over the percentage of progressor samples in the training set that have a ratio lower than the observed ratio and the percentage of control samples in the training set that have a ratio lower than the observed ratio. By separately considering the progressors and controls, the conversion of the ratio to a score is independent of the relative numbers of progressors and controls in the training population.

The procedure can be broken down into the following steps:
i) Measure the cycle thresholds (Cts) for the two, three or four primer-probes (e.g. those listed in Table 1).
ii) For each of the pairs of primer-probes, compute the difference in raw Ct, which produces the log-transformed ratio of expression.
iii) Compare the measured ratio to ratios in look-up tables for the given pair of transcripts (e.g. Tables 2-5). Find the minimal ratio in column 1 of the table that is greater than or equal to the measured ratio.
iv) Assign the corresponding score in the second column of the look-up table to the ratio. If the measured ratio is larger than all ratios in column 1 of the look-up table, then assign a score of 1 to the ratio.
v) If more than one gene pair ratio has been measured, compute the average over the scores generated from the set of pairs. If any assays failed on the sample, compute the average score over all ratios not including the failed assays. The resulting average is the final score for that sample.
vi) The score is an indication of the likelihood of the subject developing active TB, especially within the next two years. The higher the score, the higher the likelihood of the subject developing active TB. For example, a score of 0 or close to 0 indicates that the subject is highly unlikely to develop active TB, whereas a score of 1 or close to 1 indicates that the subject is highly likely to develop active TB.

The overall output of the Pair Ratio signatures is thus a score, which is the average over the scores from the individual pairs. One of the strengths of the signature is that it is robust to missing data, which often occurs in qRT-PCR measurements. If a particular assay fails on a given sample, then the score is computed by simply computing the average score from all ratios that do not involve that assay. Similarly, where a reference threshold value is used, the actual value will depend on a number of parameters, such as the TB burden in the region where the method is being applied, the resources available, the intended application (e.g. monitoring subjects who are likely to develop active TB or providing treatment to these subjects), and so forth. The score could also be adjusted so that fewer subjects are identified as being likely to progress to active TB, e.g. where treatment resources are very limited. For example, the reference threshold value can be set as 0, 0.1, 0.2, 0.3, 0.4, 0.5, 0.6, and so forth.

In Tables 2-5, the score is from 0 to 1. However, a person skilled in the art will understand that any alternative number ranges could also be used.

TABLE 2

Look-up score table for GAS6/CD1C. Scores are assigned to the first ratio (column 1) that is greater than or equal to the measured ratio

| Ratio | Score |
|---|---|
| −3.98167 | 0 |
| −3.78701 | 0.00303 |
| −3.63617 | 0.006061 |
| −3.52924 | 0.009091 |
| −3.21867 | 0.012121 |
| −3.03036 | 0.015152 |
| −2.86858 | 0.018182 |
| −2.8473 | 0.021212 |
| −2.844 | 0.024242 |
| −2.7316 | 0.033014 |
| −2.72854 | 0.036045 |
| −2.69067 | 0.039075 |
| −2.66633 | 0.042105 |
| −2.63789 | 0.045136 |
| −2.62555 | 0.048166 |
| −2.59496 | 0.051196 |
| −2.56638 | 0.054226 |
| −2.56029 | 0.057257 |
| −2.4966 | 0.066029 |
| −2.49418 | 0.069059 |
| −2.46278 | 0.072089 |
| −2.4557 | 0.07512 |
| −2.42006 | 0.07815 |
| −2.39469 | 0.08118 |
| −2.34326 | 0.084211 |
| −2.34255 | 0.087241 |
| −2.33544 | 0.090271 |
| −2.3273 | 0.093301 |
| −2.32627 | 0.096332 |
| −2.32537 | 0.099362 |
| −2.29852 | 0.102392 |
| −2.29164 | 0.105423 |
| −2.28667 | 0.108453 |
| −2.27676 | 0.111483 |
| −2.27508 | 0.120255 |
| −2.24703 | 0.123286 |
| −2.23931 | 0.126316 |
| −2.23179 | 0.129346 |
| −2.2258 | 0.132376 |
| −2.2238 | 0.135407 |
| −2.21685 | 0.144179 |
| −2.21139 | 0.152951 |
| −2.20246 | 0.161723 |
| −2.19798 | 0.164753 |
| −2.19378 | 0.167783 |
| −2.1937 | 0.170813 |
| −2.19232 | 0.173844 |
| −2.16766 | 0.176874 |
| −2.16649 | 0.179904 |
| −2.16533 | 0.182935 |
| −2.15975 | 0.185965 |
| −2.1594 | 0.188995 |
| −2.14503 | 0.192026 |
| −2.14474 | 0.195056 |
| −2.141 | 0.198086 |
| −2.13551 | 0.201116 |
| −2.12167 | 0.204147 |
| −2.11346 | 0.207177 |
| −2.11203 | 0.210207 |
| −2.10899 | 0.213238 |
| −2.09659 | 0.216268 |
| −2.09198 | 0.219298 |
| −2.08432 | 0.222329 |
| −2.08375 | 0.225359 |
| −2.08231 | 0.234131 |

TABLE 2-continued

Look-up score table for GAS6/CD1C. Scores are assigned to the first ratio (column 1) that is greater than or equal to the measured ratio

| Ratio | Score |
|---|---|
| −2.07458 | 0.237161 |
| −2.06679 | 0.240191 |
| −2.05269 | 0.243222 |
| −2.04339 | 0.246252 |
| −2.03834 | 0.249282 |
| −2.0266 | 0.252313 |
| −2.01843 | 0.255343 |
| −2.01574 | 0.258373 |
| −2.01209 | 0.261404 |
| −2.00431 | 0.264434 |
| −1.99967 | 0.267464 |
| −1.98219 | 0.270494 |
| −1.98213 | 0.273525 |
| −1.95914 | 0.282297 |
| −1.9572 | 0.285327 |
| −1.95174 | 0.288357 |
| −1.93893 | 0.291388 |
| −1.93607 | 0.294418 |
| −1.91529 | 0.297448 |
| −1.90047 | 0.300479 |
| −1.89962 | 0.303509 |
| −1.89668 | 0.306539 |
| −1.88961 | 0.315311 |
| −1.88152 | 0.318341 |
| −1.87806 | 0.327113 |
| −1.86333 | 0.330144 |
| −1.85495 | 0.333174 |
| −1.85325 | 0.341946 |
| −1.83833 | 0.344976 |
| −1.83482 | 0.348006 |
| −1.82513 | 0.351037 |
| −1.81775 | 0.354067 |
| −1.80735 | 0.357097 |
| −1.77716 | 0.360128 |
| −1.75439 | 0.363158 |
| −1.75128 | 0.366188 |
| −1.75066 | 0.37496 |
| −1.73535 | 0.37799 |
| −1.73349 | 0.381021 |
| −1.71685 | 0.384051 |
| −1.71256 | 0.387081 |
| −1.68203 | 0.395853 |
| −1.68036 | 0.398884 |
| −1.67836 | 0.401914 |
| −1.67174 | 0.404944 |
| −1.66799 | 0.413716 |
| −1.65729 | 0.422488 |
| −1.65567 | 0.425518 |
| −1.64717 | 0.428549 |
| −1.64318 | 0.431579 |
| −1.63706 | 0.434609 |
| −1.63035 | 0.43764 |
| −1.57138 | 0.446412 |
| −1.56156 | 0.449442 |
| −1.53783 | 0.452472 |
| −1.5329 | 0.455502 |
| −1.51317 | 0.458533 |
| −1.51254 | 0.461563 |
| −1.50054 | 0.470335 |
| −1.49371 | 0.473365 |
| −1.47111 | 0.476396 |
| −1.46727 | 0.479426 |
| −1.46182 | 0.482456 |
| −1.46171 | 0.485486 |
| −1.46056 | 0.488517 |
| −1.45973 | 0.491547 |
| −1.45355 | 0.494577 |
| −1.42133 | 0.497608 |
| −1.41826 | 0.500638 |
| −1.41299 | 0.503668 |
| −1.40673 | 0.506699 |
| −1.40214 | 0.509729 |
| −1.39583 | 0.518501 |
| −1.3937 | 0.527273 |
| −1.36969 | 0.530303 |
| −1.36284 | 0.533333 |
| −1.3424 | 0.536364 |
| −1.34168 | 0.539394 |
| −1.30559 | 0.542424 |
| −1.30213 | 0.545455 |
| −1.29271 | 0.548485 |
| −1.28957 | 0.551515 |
| −1.2889 | 0.560287 |
| −1.2764 | 0.563317 |
| −1.24774 | 0.566348 |
| −1.24482 | 0.569378 |
| −1.22221 | 0.572408 |
| −1.2153 | 0.575439 |
| −1.20454 | 0.578469 |
| −1.19764 | 0.587241 |
| −1.18217 | 0.590271 |
| −1.17884 | 0.593301 |
| −1.15793 | 0.596332 |
| −1.15596 | 0.599362 |
| −1.1471 | 0.608134 |
| −1.12392 | 0.616906 |
| −1.11971 | 0.619936 |
| −1.11168 | 0.622967 |
| −1.10357 | 0.631738 |
| −1.08656 | 0.634769 |
| −1.06278 | 0.643541 |
| −1.06184 | 0.652313 |
| −1.04183 | 0.655343 |
| −1.02963 | 0.658373 |
| −1.01694 | 0.661404 |
| −1.01088 | 0.664434 |
| −1.00524 | 0.667464 |
| −0.97624 | 0.670494 |
| −0.95269 | 0.679266 |
| −0.94713 | 0.688038 |
| −0.93541 | 0.69681 |
| −0.93205 | 0.699841 |
| −0.93003 | 0.708612 |
| −0.92691 | 0.717384 |
| −0.89482 | 0.726156 |
| −0.88314 | 0.729187 |
| −0.88227 | 0.732217 |
| −0.87868 | 0.735247 |
| −0.8713 | 0.744019 |
| −0.86495 | 0.747049 |
| −0.85906 | 0.755821 |
| −0.7956 | 0.764593 |
| −0.76541 | 0.773365 |
| −0.76203 | 0.776396 |
| −0.74811 | 0.785168 |
| −0.64078 | 0.788198 |
| −0.63978 | 0.79697 |
| −0.60152 | 0.8 |
| −0.60077 | 0.808772 |
| −0.59067 | 0.817544 |
| −0.56355 | 0.826316 |
| −0.52765 | 0.829346 |
| −0.5262 | 0.832376 |
| −0.50011 | 0.835407 |
| −0.44177 | 0.844179 |
| −0.43954 | 0.847209 |
| −0.40211 | 0.850239 |
| −0.37502 | 0.859011 |
| −0.28114 | 0.862042 |
| −0.22487 | 0.865072 |
| −0.18841 | 0.868102 |
| −0.17801 | 0.876874 |
| −0.16843 | 0.879904 |
| −0.13736 | 0.888676 |
| −0.07479 | 0.891707 |
| −0.05221 | 0.900479 |
| 0.078313 | 0.90925 |
| 0.162239 | 0.912281 |
| 0.264366 | 0.921053 |
| 0.291306 | 0.929825 |

TABLE 2-continued

Look-up score table for GAS6/CD1C. Scores are assigned to the first ratio (column 1) that is greater than or equal to the measured ratio

| Ratio | Score |
|---|---|
| 0.299946 | 0.938597 |
| 0.360062 | 0.947368 |
| 0.503116 | 0.95614 |
| 0.584122 | 0.964912 |
| 0.706544 | 0.973684 |
| 1.054355 | 0.982456 |
| 2.811832 | 0.991228 |

TABLE 3

Look-up score table for SEPT4/BLK. Scores are assigned to the first ratio (column 1) that is greater than or equal to the measured ratio

| Ratio | Score |
|---|---|
| −6.05352 | 0 |
| −5.69963 | 0.003049 |
| −5.65532 | 0.006098 |
| −5.43898 | 0.009146 |
| −5.05103 | 0.012195 |
| −4.77652 | 0.015244 |
| −4.76179 | 0.018293 |
| −4.6429 | 0.021341 |
| −4.62642 | 0.02439 |
| −4.60143 | 0.027439 |
| −4.52098 | 0.030488 |
| −4.3933 | 0.033537 |
| −4.38816 | 0.036585 |
| −4.37072 | 0.045357 |
| −4.37067 | 0.048406 |
| −4.31138 | 0.051455 |
| −4.2607 | 0.054504 |
| −4.25419 | 0.057552 |
| −4.2133 | 0.060601 |
| −4.16415 | 0.069373 |
| −4.14117 | 0.072422 |
| −4.12753 | 0.075471 |
| −4.12381 | 0.078519 |
| −4.08798 | 0.081568 |
| −4.08439 | 0.084617 |
| −4.08298 | 0.087666 |
| −4.07186 | 0.090715 |
| −4.05415 | 0.093763 |
| −4.00482 | 0.096812 |
| −3.99942 | 0.099861 |
| −3.9752 | 0.10291 |
| −3.95498 | 0.105959 |
| −3.94982 | 0.109007 |
| −3.92034 | 0.112056 |
| −3.90442 | 0.115105 |
| −3.82151 | 0.118154 |
| −3.78362 | 0.121202 |
| −3.7803 | 0.124251 |
| −3.7766 | 0.1273 |
| −3.77608 | 0.130349 |
| −3.77166 | 0.133398 |
| −3.76973 | 0.136446 |
| −3.69708 | 0.139495 |
| −3.6518 | 0.142544 |
| −3.64744 | 0.145593 |
| −3.6436 | 0.148641 |
| −3.63935 | 0.157413 |
| −3.63514 | 0.160462 |
| −3.6238 | 0.163511 |
| −3.62352 | 0.16656 |
| −3.60301 | 0.169609 |
| −3.53689 | 0.172657 |
| −3.52673 | 0.175706 |
| −3.52413 | 0.178755 |
| −3.5098 | 0.181804 |
| −3.50459 | 0.184852 |
| −3.49474 | 0.187901 |

TABLE 3-continued

Look-up score table for SEPT4/BLK. Scores are assigned to the first ratio (column 1) that is greater than or equal to the measured ratio

| Ratio | Score |
|---|---|
| −3.4913 | 0.19095 |
| −3.48863 | 0.193999 |
| −3.47129 | 0.202771 |
| −3.46965 | 0.205819 |
| −3.44634 | 0.208868 |
| −3.41104 | 0.211917 |
| −3.40509 | 0.214966 |
| −3.40272 | 0.218015 |
| −3.39284 | 0.221063 |
| −3.37651 | 0.229835 |
| −3.36896 | 0.232884 |
| −3.36105 | 0.235933 |
| −3.29721 | 0.244705 |
| −3.27066 | 0.247754 |
| −3.26883 | 0.250802 |
| −3.2545 | 0.253851 |
| −3.24894 | 0.2569 |
| −3.23788 | 0.259949 |
| −3.22094 | 0.262997 |
| −3.2141 | 0.266046 |
| −3.18795 | 0.269095 |
| −3.18735 | 0.272144 |
| −3.18651 | 0.275193 |
| −3.16157 | 0.278241 |
| −3.15853 | 0.28129 |
| −3.15683 | 0.284339 |
| −3.15249 | 0.293111 |
| −3.13697 | 0.301883 |
| −3.13463 | 0.304932 |
| −3.04615 | 0.30798 |
| −3.03549 | 0.316752 |
| −3.00268 | 0.319801 |
| −2.98559 | 0.32285 |
| −2.98363 | 0.325899 |
| −2.95543 | 0.328947 |
| −2.94437 | 0.331996 |
| −2.94286 | 0.335045 |
| −2.93692 | 0.338094 |
| −2.91765 | 0.341143 |
| −2.90589 | 0.344191 |
| −2.89195 | 0.34724 |
| −2.88996 | 0.350289 |
| −2.87672 | 0.353338 |
| −2.87106 | 0.36211 |
| −2.85189 | 0.365158 |
| −2.84325 | 0.368207 |
| −2.83989 | 0.376979 |
| −2.81943 | 0.385751 |
| −2.77316 | 0.3888 |
| −2.76854 | 0.397572 |
| −2.74809 | 0.400621 |
| −2.72424 | 0.403669 |
| −2.71122 | 0.406718 |
| −2.69437 | 0.409767 |
| −2.68981 | 0.412816 |
| −2.67909 | 0.421588 |
| −2.67393 | 0.430359 |
| −2.67289 | 0.433408 |
| −2.66145 | 0.44218 |
| −2.64115 | 0.445229 |
| −2.61911 | 0.454001 |
| −2.59863 | 0.45705 |
| −2.59846 | 0.460098 |
| −2.59013 | 0.463147 |
| −2.58633 | 0.466196 |
| −2.55749 | 0.474968 |
| −2.55196 | 0.478017 |
| −2.52197 | 0.481066 |
| −2.49778 | 0.484114 |
| −2.48238 | 0.487163 |
| −2.47791 | 0.490212 |
| −2.46764 | 0.493261 |
| −2.46032 | 0.496309 |
| −2.44661 | 0.505081 |
| −2.42836 | 0.513853 |

TABLE 3-continued

Look-up score table for SEPT4/BLK. Scores are assigned to the first ratio (column 1) that is greater than or equal to the measured ratio

| Ratio | Score |
| --- | --- |
| −2.42413 | 0.522625 |
| −2.41727 | 0.525674 |
| −2.39692 | 0.534446 |
| −2.39646 | 0.537495 |
| −2.37823 | 0.540543 |
| −2.33909 | 0.549315 |
| −2.31861 | 0.558087 |
| −2.31655 | 0.566859 |
| −2.29876 | 0.569908 |
| −2.27299 | 0.572957 |
| −2.26615 | 0.581729 |
| −2.2595 | 0.584778 |
| −2.25733 | 0.587826 |
| −2.24599 | 0.590875 |
| −2.23917 | 0.599647 |
| −2.12637 | 0.602696 |
| −2.11029 | 0.605745 |
| −2.11013 | 0.608793 |
| −2.10399 | 0.611842 |
| −2.10043 | 0.614891 |
| −2.089 | 0.61794 |
| −2.01473 | 0.620988 |
| −2.0135 | 0.624037 |
| −2.00978 | 0.627086 |
| −1.95195 | 0.630135 |
| −1.95066 | 0.633184 |
| −1.92764 | 0.636232 |
| −1.92277 | 0.639281 |
| −1.91245 | 0.64233 |
| −1.90725 | 0.651102 |
| −1.88741 | 0.654151 |
| −1.88356 | 0.657199 |
| −1.87923 | 0.660248 |
| −1.8655 | 0.663297 |
| −1.85247 | 0.666346 |
| −1.8471 | 0.669395 |
| −1.83659 | 0.672443 |
| −1.83514 | 0.675492 |
| −1.8321 | 0.684264 |
| −1.83015 | 0.687313 |
| −1.80585 | 0.690362 |
| −1.80099 | 0.69341 |
| −1.74966 | 0.696459 |
| −1.72589 | 0.705231 |
| −1.71738 | 0.70828 |
| −1.71361 | 0.711329 |
| −1.70456 | 0.720101 |
| −1.65859 | 0.723149 |
| −1.6173 | 0.726198 |
| −1.5977 | 0.729247 |
| −1.59287 | 0.732296 |
| −1.50914 | 0.741068 |
| −1.50599 | 0.74984 |
| −1.50586 | 0.752888 |
| −1.49608 | 0.755937 |
| −1.49388 | 0.758986 |
| −1.48775 | 0.767758 |
| −1.46569 | 0.770807 |
| −1.46267 | 0.779579 |
| −1.42746 | 0.782627 |
| −1.41471 | 0.791399 |
| −1.24309 | 0.800171 |
| −1.14306 | 0.80322 |
| −1.07721 | 0.811992 |
| −0.99861 | 0.815041 |
| −0.96411 | 0.818089 |
| −0.90503 | 0.826861 |
| −0.78205 | 0.82991 |
| −0.77843 | 0.838682 |
| −0.70912 | 0.847454 |
| −0.58869 | 0.856226 |
| −0.58661 | 0.864998 |
| −0.46978 | 0.87377 |
| −0.42427 | 0.882542 |
| −0.34341 | 0.891314 |
| −0.32003 | 0.900086 |
| −0.29162 | 0.903134 |
| −0.14455 | 0.911906 |
| 0.027955 | 0.920678 |
| 0.045947 | 0.92945 |
| 0.071005 | 0.932499 |
| 0.175041 | 0.941271 |
| 0.185004 | 0.950043 |
| 0.482942 | 0.953092 |
| 1.277772 | 0.95614 |
| 1.763216 | 0.964912 |
| 2.260903 | 0.973684 |
| 2.515072 | 0.982456 |
| 3.639134 | 0.991228 |

TABLE 4

Look-up score table for SEPT4/CD1C. Scores are assigned to the first ratio (column 1) that is greater than or equal to the measured ratio

| Ratio | Score |
| --- | --- |
| −4.26676 | 0 |
| −3.90412 | 0.003049 |
| −3.57322 | 0.006098 |
| −3.48961 | 0.009146 |
| −3.46851 | 0.012195 |
| −3.45242 | 0.015244 |
| −3.44606 | 0.018293 |
| −3.43129 | 0.021341 |
| −3.43014 | 0.02439 |
| −3.30163 | 0.027439 |
| −3.28282 | 0.030488 |
| −3.25011 | 0.033537 |
| −3.24878 | 0.036585 |
| −3.11992 | 0.039634 |
| −3.0962 | 0.048406 |
| −2.89213 | 0.051455 |
| −2.85606 | 0.054504 |
| −2.85501 | 0.057552 |
| −2.81683 | 0.060601 |
| −2.81423 | 0.06365 |
| −2.80929 | 0.066699 |
| −2.80449 | 0.069748 |
| −2.79271 | 0.072796 |
| −2.77478 | 0.075845 |
| −2.77462 | 0.078894 |
| −2.77421 | 0.081943 |
| −2.72136 | 0.084991 |
| −2.6961 | 0.08804 |
| −2.65229 | 0.091089 |
| −2.53896 | 0.094138 |
| −2.4878 | 0.097187 |
| −2.48247 | 0.100235 |
| −2.47041 | 0.109007 |
| −2.44189 | 0.112056 |
| −2.41416 | 0.115105 |
| −2.41022 | 0.118154 |
| −2.40696 | 0.121202 |
| −2.35745 | 0.124251 |
| −2.35387 | 0.133023 |
| −2.34588 | 0.136072 |
| −2.3419 | 0.139121 |
| −2.32414 | 0.142169 |
| −2.31969 | 0.145218 |
| −2.31044 | 0.148267 |
| −2.29575 | 0.151316 |
| −2.27892 | 0.154365 |
| −2.27281 | 0.163137 |
| −2.25735 | 0.166185 |
| −2.25153 | 0.169234 |
| −2.25054 | 0.172283 |

TABLE 4-continued

Look-up score table for SEPT4/CD1C. Scores are assigned to the first ratio (column 1) that is greater than or equal to the measured ratio

| Ratio | Score |
|---|---|
| −2.23755 | 0.181055 |
| −2.2357 | 0.184104 |
| −2.22661 | 0.187152 |
| −2.2082 | 0.190201 |
| −2.20435 | 0.19325 |
| −2.20289 | 0.196299 |
| −2.19718 | 0.199348 |
| −2.1702 | 0.202396 |
| −2.15131 | 0.205445 |
| −2.13672 | 0.208494 |
| −2.13081 | 0.211543 |
| −2.12689 | 0.214591 |
| −2.12149 | 0.21764 |
| −2.11194 | 0.220689 |
| −2.08411 | 0.223738 |
| −2.07491 | 0.226787 |
| −2.07471 | 0.229835 |
| −2.0711 | 0.232884 |
| −2.03434 | 0.241656 |
| −2.02584 | 0.244705 |
| −2.01479 | 0.247754 |
| −2.00107 | 0.250802 |
| −1.96434 | 0.253851 |
| −1.95458 | 0.2569 |
| −1.94124 | 0.259949 |
| −1.91667 | 0.262997 |
| −1.90277 | 0.266046 |
| −1.8607 | 0.269095 |
| −1.84867 | 0.272144 |
| −1.82525 | 0.275193 |
| −1.81575 | 0.278241 |
| −1.81185 | 0.28129 |
| −1.81164 | 0.290062 |
| −1.78693 | 0.293111 |
| −1.77913 | 0.29616 |
| −1.77287 | 0.299208 |
| −1.7509 | 0.302257 |
| −1.74851 | 0.305306 |
| −1.73305 | 0.308355 |
| −1.73264 | 0.311404 |
| −1.72665 | 0.320175 |
| −1.71098 | 0.328947 |
| −1.70611 | 0.331996 |
| −1.70569 | 0.335045 |
| −1.7034 | 0.338094 |
| −1.70289 | 0.346866 |
| −1.69956 | 0.349914 |
| −1.69458 | 0.352963 |
| −1.69226 | 0.361735 |
| −1.68816 | 0.364784 |
| −1.67806 | 0.367833 |
| −1.65632 | 0.376605 |
| −1.65194 | 0.379653 |
| −1.65049 | 0.388425 |
| −1.64809 | 0.391474 |
| −1.61323 | 0.394523 |
| −1.60107 | 0.397572 |
| −1.59417 | 0.400621 |
| −1.58737 | 0.403669 |
| −1.58144 | 0.406718 |
| −1.57835 | 0.409767 |
| −1.56482 | 0.418539 |
| −1.55752 | 0.421588 |
| −1.54618 | 0.424636 |
| −1.52674 | 0.427685 |
| −1.52291 | 0.430734 |
| −1.51931 | 0.433783 |
| −1.51588 | 0.436831 |
| −1.51213 | 0.43988 |
| −1.50251 | 0.442929 |
| −1.46527 | 0.445978 |
| −1.46221 | 0.45475 |
| −1.43942 | 0.457799 |
| −1.43906 | 0.460847 |
| −1.43724 | 0.463896 |
| −1.38933 | 0.472668 |
| −1.37654 | 0.48144 |
| −1.36041 | 0.484489 |
| −1.35432 | 0.487537 |
| −1.35196 | 0.496309 |
| −1.34998 | 0.499358 |
| −1.3222 | 0.502407 |
| −1.31737 | 0.505456 |
| −1.30434 | 0.508505 |
| −1.30192 | 0.511553 |
| −1.29485 | 0.520325 |
| −1.29338 | 0.529097 |
| −1.28993 | 0.537869 |
| −1.28597 | 0.540918 |
| −1.28597 | 0.543967 |
| −1.27254 | 0.552739 |
| −1.26016 | 0.555787 |
| −1.23334 | 0.558836 |
| −1.22627 | 0.561885 |
| −1.21048 | 0.564934 |
| −1.17263 | 0.573706 |
| −1.16768 | 0.582478 |
| −1.14209 | 0.585526 |
| −1.13872 | 0.588575 |
| −1.11203 | 0.591624 |
| −1.09822 | 0.594673 |
| −1.0945 | 0.603445 |
| −1.07973 | 0.606493 |
| −1.02027 | 0.609542 |
| −1.01793 | 0.612591 |
| −1.0006 | 0.61564 |
| −1.00007 | 0.624412 |
| −0.97571 | 0.633184 |
| −0.9355 | 0.641956 |
| −0.92824 | 0.645004 |
| −0.92374 | 0.648053 |
| −0.91832 | 0.651102 |
| −0.91572 | 0.654151 |
| −0.91439 | 0.657199 |
| −0.9072 | 0.660248 |
| −0.89902 | 0.663297 |
| −0.89429 | 0.666346 |
| −0.88043 | 0.669395 |
| −0.87544 | 0.678167 |
| −0.86052 | 0.681215 |
| −0.82631 | 0.689987 |
| −0.81442 | 0.698759 |
| −0.80764 | 0.707531 |
| −0.77121 | 0.716303 |
| −0.74853 | 0.719352 |
| −0.73739 | 0.728124 |
| −0.72368 | 0.731172 |
| −0.71231 | 0.734221 |
| −0.70009 | 0.742993 |
| −0.69688 | 0.751765 |
| −0.68822 | 0.754814 |
| −0.68648 | 0.757863 |
| −0.68045 | 0.760911 |
| −0.68044 | 0.76396 |
| −0.65261 | 0.767009 |
| −0.64388 | 0.770058 |
| −0.6337 | 0.773107 |
| −0.60858 | 0.776155 |
| −0.50719 | 0.779204 |
| −0.42545 | 0.787976 |
| −0.40529 | 0.796748 |
| −0.25711 | 0.799797 |
| −0.20064 | 0.802846 |
| −0.17995 | 0.805894 |
| −0.12525 | 0.808943 |
| −0.08058 | 0.811992 |
| 0.007699 | 0.820764 |
| 0.04189 | 0.823813 |
| 0.081355 | 0.832585 |
| 0.210153 | 0.835633 |

TABLE 4-continued

Look-up score table for SEPT4/CD1C. Scores are assigned to the first ratio (column 1) that is greater than or equal to the measured ratio

| Ratio | Score |
|---|---|
| 0.372822 | 0.838682 |
| 0.47311 | 0.847454 |
| 0.573476 | 0.850503 |
| 0.634893 | 0.853552 |
| 0.849913 | 0.862324 |
| 1.005702 | 0.871095 |
| 1.070146 | 0.879867 |
| 1.090074 | 0.888639 |
| 1.13166 | 0.897411 |
| 1.157755 | 0.906183 |
| 1.273086 | 0.914955 |
| 1.379731 | 0.923727 |
| 1.469716 | 0.932499 |
| 1.898259 | 0.941271 |
| 1.979775 | 0.950043 |
| 2.150658 | 0.953092 |
| 2.22947 | 0.961864 |
| 2.63822 | 0.964912 |
| 3.122758 | 0.973684 |
| 3.221994 | 0.982456 |
| 4.53438 | 0.991228 |

TABLE 5

Look-up score table for GAS6/BLK. Scores are assigned to the first ratio (column 1) that is greater than or equal to the measured ratio

| Ratio | Score |
|---|---|
| −5.46159 | 0 |
| −5.32474 | 0.00303 |
| −4.99779 | 0.006061 |
| −4.77011 | 0.009091 |
| −4.6801 | 0.012121 |
| −4.58959 | 0.015152 |
| −4.5499 | 0.018182 |
| −4.45435 | 0.026954 |
| −4.19505 | 0.029984 |
| −4.1727 | 0.033014 |
| −4.14232 | 0.036045 |
| −4.1322 | 0.039075 |
| −4.12432 | 0.042105 |
| −4.07146 | 0.050877 |
| −4.0584 | 0.053908 |
| −4.03279 | 0.056938 |
| −4.02077 | 0.059968 |
| −3.98267 | 0.062998 |
| −3.91316 | 0.07177 |
| −3.90179 | 0.074801 |
| −3.87165 | 0.077831 |
| −3.85668 | 0.080861 |
| −3.81792 | 0.083892 |
| −3.81183 | 0.086922 |
| −3.7746 | 0.089952 |
| −3.69745 | 0.092982 |
| −3.69361 | 0.096013 |
| −3.66887 | 0.099043 |
| −3.66341 | 0.102073 |
| −3.63178 | 0.105104 |
| −3.62407 | 0.108134 |
| −3.61784 | 0.111164 |
| −3.61404 | 0.114195 |
| −3.6112 | 0.117225 |
| −3.5826 | 0.120255 |
| −3.57608 | 0.123286 |
| −3.56735 | 0.126316 |
| −3.56211 | 0.129346 |
| −3.54654 | 0.132376 |
| −3.54651 | 0.135407 |
| −3.53642 | 0.144179 |
| −3.53312 | 0.147209 |
| −3.52847 | 0.150239 |

TABLE 5-continued

Look-up score table for GAS6/BLK. Scores are assigned to the first ratio (column 1) that is greater than or equal to the measured ratio

| Ratio | Score |
|---|---|
| −3.52332 | 0.15327 |
| −3.50901 | 0.1563 |
| −3.49654 | 0.15933 |
| −3.48307 | 0.16236 |
| −3.47284 | 0.165391 |
| −3.47281 | 0.168421 |
| −3.46952 | 0.171451 |
| −3.46201 | 0.174482 |
| −3.45861 | 0.177512 |
| −3.43378 | 0.180542 |
| −3.39236 | 0.183573 |
| −3.3884 | 0.186603 |
| −3.38373 | 0.189633 |
| −3.37906 | 0.192664 |
| −3.37846 | 0.201435 |
| −3.37843 | 0.204466 |
| −3.36582 | 0.207496 |
| −3.35906 | 0.210526 |
| −3.35745 | 0.213557 |
| −3.35185 | 0.216587 |
| −3.35172 | 0.219617 |
| −3.35011 | 0.222648 |
| −3.31812 | 0.225678 |
| −3.31135 | 0.228708 |
| −3.29154 | 0.231738 |
| −3.28842 | 0.234769 |
| −3.287 | 0.237799 |
| −3.27898 | 0.240829 |
| −3.25776 | 0.24386 |
| −3.25395 | 0.24689 |
| −3.23294 | 0.24992 |
| −3.2224 | 0.252951 |
| −3.21114 | 0.255981 |
| −3.20628 | 0.259011 |
| −3.20283 | 0.267783 |
| −3.20165 | 0.270813 |
| −3.20133 | 0.273844 |
| −3.19848 | 0.276874 |
| −3.19744 | 0.285646 |
| −3.16121 | 0.288676 |
| −3.16049 | 0.297448 |
| −3.15388 | 0.300479 |
| −3.13557 | 0.30925 |
| −3.10031 | 0.312281 |
| −3.09072 | 0.315311 |
| −3.08963 | 0.324083 |
| −3.08767 | 0.327113 |
| −3.07193 | 0.335885 |
| −3.06867 | 0.338916 |
| −3.04044 | 0.341946 |
| −3.02851 | 0.344976 |
| −3.02829 | 0.348006 |
| −3.01804 | 0.351037 |
| −3.01428 | 0.359809 |
| −2.98776 | 0.362839 |
| −2.98629 | 0.365869 |
| −2.97774 | 0.3689 |
| −2.9372 | 0.37193 |
| −2.93127 | 0.380702 |
| −2.92491 | 0.383732 |
| −2.89711 | 0.386762 |
| −2.87735 | 0.389793 |
| −2.86923 | 0.392823 |
| −2.85323 | 0.395853 |
| −2.85224 | 0.398884 |
| −2.84782 | 0.401914 |
| −2.84736 | 0.404944 |
| −2.84414 | 0.407975 |
| −2.8408 | 0.411005 |
| −2.83336 | 0.414035 |
| −2.83306 | 0.422807 |
| −2.82234 | 0.431579 |
| −2.82025 | 0.434609 |
| −2.77864 | 0.43764 |
| −2.76621 | 0.44067 |

TABLE 5-continued

Look-up score table for GAS6/BLK. Scores are assigned to the first ratio (column 1) that is greater than or equal to the measured ratio

| Ratio | Score |
|---|---|
| −2.74251 | 0.4437 |
| −2.73508 | 0.452472 |
| −2.72591 | 0.461244 |
| −2.72073 | 0.464274 |
| −2.71932 | 0.473046 |
| −2.71446 | 0.476077 |
| −2.69913 | 0.479107 |
| −2.6919 | 0.487879 |
| −2.67408 | 0.490909 |
| −2.67257 | 0.493939 |
| −2.6721 | 0.49697 |
| −2.66926 | 0.5 |
| −2.66267 | 0.50303 |
| −2.6557 | 0.506061 |
| −2.6267 | 0.514833 |
| −2.59015 | 0.517863 |
| −2.57602 | 0.520893 |
| −2.57083 | 0.523923 |
| −2.54763 | 0.526954 |
| −2.5232 | 0.529984 |
| −2.51972 | 0.533014 |
| −2.51431 | 0.541786 |
| −2.51069 | 0.550558 |
| −2.50149 | 0.553589 |
| −2.5 | 0.556619 |
| −2.49445 | 0.559649 |
| −2.48921 | 0.568421 |
| −2.47607 | 0.571451 |
| −2.47039 | 0.580223 |
| −2.46809 | 0.583254 |
| −2.40543 | 0.586284 |
| −2.40226 | 0.589314 |
| −2.39463 | 0.592345 |
| −2.38528 | 0.595375 |
| −2.38147 | 0.598405 |
| −2.37244 | 0.601435 |
| −2.36866 | 0.604466 |
| −2.36568 | 0.607496 |
| −2.35332 | 0.616268 |
| −2.32507 | 0.619298 |
| −2.31052 | 0.62807 |
| −2.27778 | 0.636842 |
| −2.27137 | 0.639872 |
| −2.26272 | 0.642903 |
| −2.26096 | 0.651675 |
| −2.22589 | 0.654705 |
| −2.20428 | 0.657735 |
| −2.18815 | 0.660766 |
| −2.16217 | 0.663796 |
| −2.16039 | 0.672568 |
| −2.1335 | 0.675598 |
| −2.13219 | 0.678628 |
| −2.11837 | 0.681659 |
| −2.10876 | 0.684689 |
| −2.10521 | 0.687719 |
| −2.06091 | 0.69075 |
| −2.0502 | 0.69378 |
| −2.03951 | 0.69681 |
| −2.03429 | 0.699841 |
| −1.99594 | 0.708612 |
| −1.99526 | 0.711643 |
| −1.98942 | 0.720415 |
| −1.93213 | 0.729187 |
| −1.9019 | 0.732217 |
| −1.89651 | 0.735247 |
| −1.88667 | 0.744019 |
| −1.87943 | 0.747049 |
| −1.85489 | 0.75008 |
| −1.79081 | 0.758852 |
| −1.78918 | 0.767624 |
| −1.7677 | 0.770654 |
| −1.76074 | 0.773684 |
| −1.72292 | 0.782456 |
| −1.71138 | 0.791228 |
| −1.68752 | 0.794258 |
| −1.6248 | 0.80303 |
| −1.60547 | 0.811802 |
| −1.60171 | 0.814833 |
| −1.59859 | 0.823605 |
| −1.59731 | 0.826635 |
| −1.53358 | 0.835407 |
| −1.45674 | 0.838437 |
| −1.43791 | 0.841467 |
| −1.41971 | 0.844498 |
| −1.3982 | 0.847528 |
| −1.36662 | 0.8563 |
| −1.36357 | 0.85933 |
| −1.35867 | 0.86236 |
| −1.29654 | 0.871132 |
| −1.22407 | 0.879904 |
| −1.22084 | 0.888676 |
| −1.18781 | 0.897448 |
| −1.01178 | 0.900479 |
| −1.00837 | 0.90925 |
| −0.90405 | 0.918022 |
| −0.76852 | 0.926794 |
| −0.73476 | 0.935566 |
| −0.57055 | 0.944338 |
| −0.43703 | 0.95311 |
| −0.36411 | 0.961882 |
| −0.36259 | 0.964912 |
| −0.35612 | 0.973684 |
| 0.792524 | 0.982456 |
| 0.948701 | 0.991228 |

In alternative embodiments of the invention, expression levels of C1QC and TRAV27 and/or ANKRD22 and OSBPL10 can be measured and the ratio of expression of these genes can be calculated as per the Pair Ratio approach described above, to identify the likelihood of a latent tuberculosis (TB) infection in a subject transitioning to active TB disease. The expression of C1QC and ANKRD22 are upregulated and the expression of TRAV27 and OSBPL10 are downregulated during TB progression.

Development of the gene signature, referred to herein as the "RISK4" signature, is described in more detail below.

Methods

Study Design and Participants

The Bill and Melinda Gates Grand Challenges in Global Health GC6-74 project ("GC6-74") was initiated in 2003 with the goal to identify TB biomarkers with prognostic potential. The study encompassed almost 4,500 HIV-participants across four African sites: South Africa, The Gambia, Ethiopia and Uganda (FIG. 1), reflecting different regions and ethnicities. All participants were household contacts (HHC) of newly diagnosed TB index cases and were followed for two years, with blood samples taken at enrolment/baseline, 6 and 18 months (with the exception of South Africa, where PAXgene blood RNA samples were collected at baseline and 18 months of follow-up, due to logistical limitations). Index TB cases were at least 15 years old, with confirmed positive sputum smear for acid-fast bacilli, diagnosed two months or less before enrolment of the HHC. All analyzed blood samples from HHC were collected before TB diagnosis and therefore represent clinically healthy individuals. This design provided a unique opportunity to investigate the prospective risk of TB in exposed individuals, and the collection of samples from South, West and East African field sites allowed for comparisons between sites and development of a pan-African biosignature.

Overall, 79 progressors (who developed tuberculosis between 3 and 24 months following exposure) and 328 matched non-progressors (who remained healthy during 24 months of follow-up) were investigated. TB incidence in HIV-negative healthy HHC was highest in South Africa, and lowest in Ethiopia (Table 6), as defined by TB case classifications A-K in Table 7. Incident cases (progressors) were defined as those who developed TB between 3 and 24 months following exposure. "Co-incident" cases (i.e. diagnosed with TB within 3 months of contact with the index case) were not included in analysis so as to prevent inclusion of those with undiagnosed TB disease at time of exposure as progressors. Prior TB was an exclusion criterion, and thus progressors likely had their first TB episode during follow-up. Each progressor was matched to 4 HHC non-progressors/controls, who remained healthy during follow-up, by site, age category, sex, and wherever possible, year of recruitment (classifications R and S, Table 7). Age was sub-divided into 4 categories: <18, 18-25, 25-36, and >36 years of age. Approximately 3% of recruited individuals progressed to TB while the rest remained asymptomatic until the end of the two year observation period (controls). Median age of progressors was comparable across the 4 African sites (Kruskal-Wallis p=0.92, Table 8). Median times to progression were 7 months in South Africa and Uganda, and 10.5 and 10 months in The Gambia and Ethiopia, respectively (Table 6). Progressors, as defined by clinical symptoms, chest and other radiographs (CXR) consistent with TB and response to chemotherapy, without microbiological confirmation comprised 25% (4/12) of progressors in Ethiopia, 2% (1/43) in South Africa and 6% (3/34) in The Gambia (TB classification K, Table 7).

TABLE 6

Baseline demographic characteristics of progressors enrolled and matched non-progressor controls in the 4 African household contact cohorts. n: number of individuals, IQR: interquartile range

| Site | South Africa | The Gambia | Ethiopia | Uganda |
| --- | --- | --- | --- | --- |
| HIV- HHC, n | 1,197 | 1,948 | 818 | 499 |
| Progressors, n | 43 | 34 | 12 | 11 |
| Incidence, % | 3.6 | 1.7 | 1.5 | 2.2 |
| Median age, years (IQR) | | | | |
| Progressors | 25 (18-41) | 22.5 (20-30.75) | 23 (19.75-27) | 23 (18-36) |
| Non-progressors | 24 (18-38) | 24 (18-30.25) | 25 (20-35) | 27 (19-38.75) |
| Male, % | | | | |
| Progressors | 41.9 | 44.1 | 33.3 | 54.5 |
| Non-progressors | 40.7 | 44.1 | 35.4 | 54.5 |
| Median time to TB, months (IQR) | | | | |
| Progressors | 7 (5-17) | 10.5 (7-18.75) | 10 (6.5-15) | 7 (5-11) |

TABLE 7

Criteria for tuberculosis diagnosis in GC6-74 progressors

| Category | Culture 1 | Culture 2* | AFB 1 | AFB 2* | CXR | Symptoms | TB Treatment Response | Failed AB | Diagnostic Class |
| --- | --- | --- | --- | --- | --- | --- | --- | --- | --- |
| A | + | + | | | | | | | Definite |
| B | + | | | | + | | | | Definite |
| C | + | | + | | | | | | Definite |
| D | | | + | + | + | | | | Probable |
| E | | | + | + | | + | | | Probable |
| F | | | + | | + | | | | Probable |
| G | + | | | | | + | + | | Probable |
| H | + | | | | | + | | | Possible |
| I | | | + | + | | | + | | Possible |
| J | | | + | | | + | | | Possible |
| K | | | | | + | + | + | + | Possible |
| L | + | | | | | | | | Questionable |
| M | | | + | + | | | | | Questionable |
| N | | | + | | | | | | Questionable |
| O | | | | | + | + | | | Questionable |
| P | | | | | + | | | | Questionable |
| Q | | | | | | + | | | Questionable |
| R | Neg/ND | Neg/ND | Neg/ND | Neg/ND | Neg/ND | + | Rx not started | | Non-TB case |
| S | Neg/ND | Neg/ND | Neg/ND | Neg/ND | Neg/ND | Neg/ND | Rx not started | | Non-TB case |

Culture Either liquid or solid agar positive with confirmed speciation for M. tuberculosis complex
AFB Acid-fast bacilli: sputum smear ≥ scanty (≥1-9 acid-fast organisms per 100x oil field)
CXR Chest X-ray compatible with active TB
Failed AB Failed antibiotics treatment; no response of symptoms to a 7-day, broad spectrum oral or IV antibiotics
*Positivity on a separate sample of culture or AFB (not an aliquot of the same sample) provided by the participant preferrably but not necessarily on separate days
Note:
Questionable classification is excluded in both progressors and non-progressors All clinical sites adhered to the Declaration of Helsinki and Good Clinical Practice guidelines. Ethical approvals were obtained from institutional review boards. Adult participants or legal guardians of participants aged 10-17 years old provided written or thumb-printed informed consent to participate after careful explanation of the study and potential risks.

The Adolescent Cohort Study (ACS) was described previously[1,2] and included IGRA+ and/or TST+ South African adolescents aged 12-18 years old with M.tb infection, occurring at unspecified times.

RNA sequencing, polymerase chain reaction (PCR) and the Pair Ratio algorithm were employed in a training/test set approach.

Sample Processing and RNA-Sequencing

RNA was extracted from blood RNA samples using the PAXgene Blood RNA kit (Qiagen, Germantown, Md., USA), and separated into aliquots for local quality control, RNA-sequencing and qRT-PCR. Quantification of RNA and initial quality control were performed using a NanoDrop 2000™ spectrophotometer (ThermoFisher Scientific, Waltham, Mass., USA), followed by Agilent 2100 Bioanalyzer sampling (Agilent, Santa Clara, Calif., USA) to determine RNA Integrity. RNA samples with a minimum of 200 ng total RNA and RNA integrity number were submitted for sequencing (see FIG. 6 for QC exclusions).

For RNA-sequencing, globin transcript depletion (GlobinClear, ThermoFisher Scientific, MA, USA), cDNA library preparation (Illumina TruSeq Stranded mRNA; Illumina, CA, USA)), and RNA sequencing (60 million 50 bp paired-end reads on HiSeq-4000 sequencers) were performed by Beijing Genomics Institute (Shenzhen, China). FASTQ files were deposited into the Gene Expression Omnibus[26] under accession GSE94438.

Quality Control and Processing of RNA-Seq Data:

Read pairs were preprocessed by adjusting base calls with phred scores <5 to 'N' and removing for which either end had fewer than 30 unambiguous base calls. Read pairs were aligned to the human genome (hg19) using STAR (v2.3.1d) [5], taking as input the Ensembl GRCh37.74 splice junction table and allowing for novel splice junction detection. Gene expression was quantified in terms of splice junction counts to facilitate inter-conversion between RNA-Seq and qRT-PCR platforms, as previously described[3]. Junction-level expression values were standardized for each sample using a set of reference features, such that:

$$abundance_j = \log_2(counts_j + 1) - \sum_{r \in refs} \frac{\log_2(counts_r + 1)}{N_{refs}}$$

where abundance is the standardized estimate of abundance for junction j, counts, is the raw number of reads aligning to junction I, and $N_{refs}$ is the number of reference junctions used for standardization (here, $N_{refs}$=20).

Quantitative Real-Time PCR (qRT-PCR):

Expression levels of genes of interest were analyzed by qRT-PCR using Taqman FAM-TAMRA gene expression primer-probe assays (Thermo Fisher Scientific, Waltham, Mass.) mapping to splice junctions selected by machine learning analysis. cDNA was synthesized using Superscript II reverse transcriptase (Thermo Fisher Scientific), followed by pre-amplification with primer-probe master mixes of 96 assays run on each chip as follows: 95° C. for 10 minutes followed by 16 cycles of: 95° C. for 15 seconds, then 60 minutes for 4 minutes and cooled to 4° C. Multiplex qRT-PCR reactions were performed on the BioMark HD (Fluidigm, San Francisco, Calif.) using microfluidic 96.96 gene expression chips (Fluidigm). Reaction Ct values were generated using Fluidigm Real-time PCR Analysis Software v.3.1.3 (Fluidigm), with a quality threshold of 0.65, linear derivative baseline correction method and auto global setting for Ct threshold determination.

For the RNA-seq discovery of the South Africa and Gambia signatures, pair selection for inclusion in the final signature was performed in a two-step procedure. First, all exon-exon junctions were evaluated at the univariate level for the ability to predict progression. Due to the imbalance in progressors and non-progressors in the training sets, 500 re-sampled training sets were formed for both sites, each including all progressor samples plus one randomly-selected matching non-progressor sample for each. For each re-sampled training set, the ability of each junction to predict progression was evaluated using the Wilcoxon test, and those junctions with a sufficiently strong signal were carried forward to the pairwise selection step. The univariate selection criterion in South Africa was all junctions that had Wilcoxon p<0.001 in at least 70% of the re-sampled training sets, and in The Gambia the criterion was all junctions with Wilcoxon p<0.001 in at least 80% of re-sampled training sets. These cutoffs were determined by optimizing Leave-One-Out-Cross-Validation (LOOCV) results. Once a pool of exon-exon junctions was established through the univariate selection procedure, all possible pairs of junctions (where each pair involves one junction up-regulated and one junction down-regulated during progression) were formed, and their log-ratios computed. The ability of each junction pair to predict progression was measured in terms of sensitivity and specificity. All pairs with sensitivity and specificity above a fixed cutoff were included in the final ensemble. In South Africa, the pairwise cut-off was 80%, whereas in the Gambia it was 75%. Once again, the values of these cutoffs were determined by optimizing LOOCV performance.

For the final qRT-PCR based RISK4 signature, the pool of transcripts that formed the basis of the pairwise analysis comprised all transcripts selected in the South African and Gambian RNA-seq signatures. The final ensemble was then systematically constructed.

Adaptation of RNA-Seq Signatures to qRT-PCR

Taqman primer-probe assays were selected corresponding to all splice junctions in the signatures, when possible. Pairwise linear discriminant models were trained using the qRT-PCR Cts for all of the pairs in the signatures in a direct search analogous to the method described above. Pairs including a junction without an available qRT-PCR assay were omitted.

Adaptation of Published Diagnostic Signatures to qRT-PCR

The previously published signatures from Maertzdorf et al[4] and Sweeney et al[5] were adapted to the qRT-PCR platform, and are referred to herein as DIAG4 and DIAG3, respectively. Primer-probe sets were selected for each gene in the respective signatures, and overall scores were computed for each sample as the difference in the mean of the up-regulated and the down-regulated transcripts.

Results

Figure 2:
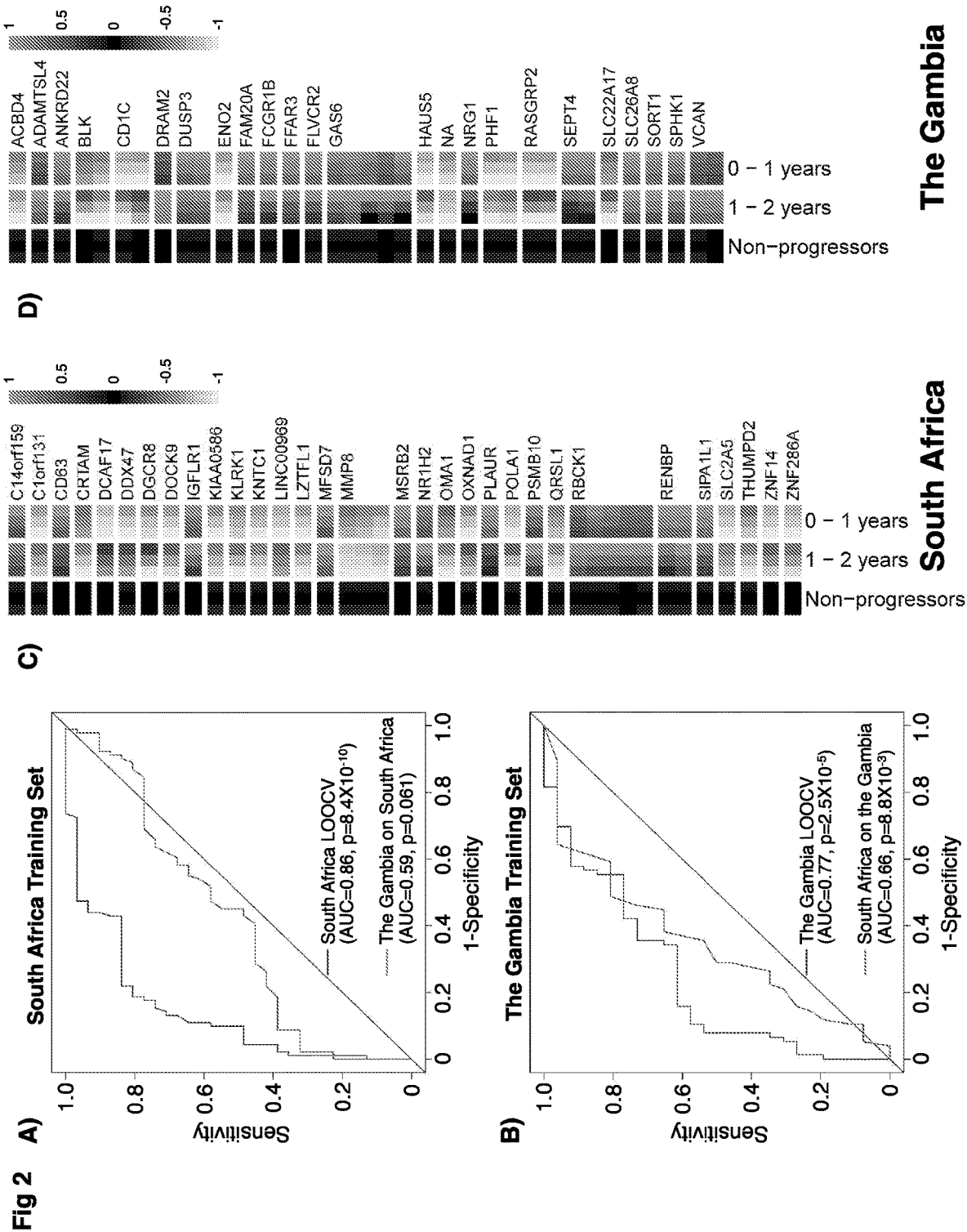
FIG. 2: Site-specific feature selection and translation to RT-PCR. (A) Receiver Operating Characteristic (ROC) Curve for Leave-One-Out Cross-Validation (LOOCV) of South Africa (blue; AUC=0.86 [0.79-0.94], $p=8.4 \times 10^{-10}$) vs. The Gambia-trained prospective signature (red; AUC=0.59 [95% CI: 0.46-0.73], p=0.06) in South African training set. (B) ROC curves for LOOCV of The Gambia (blue; AUC=0.77 [0.66-0.88], $p=2.5 \times 10^{-5}$) vs. South Africa prospective signature (red; AUC=0.66 [0.54-0.77], $p=8.8 \times 10^{-3}$) in The Gambia training set containing 26 progressor and 76 non-progressor samples. (C and D) Heatmaps showing the expression of each splice junction in the South Africa (C) and The Gambia (D) signatures in non-progressors (left columns), progressors 1-2 years before diagnosis (middle columns), and progressors 0-1 years before diagnosis (right columns). For each group of samples, the central column is the mean fold expression change vs non-progressors, while left/right columns in each group correspond to mean−/+ standard error of the mean. Each row corresponds to a splice junction, and genes with multiple rows are represented by multiple splice junctions in the signature.
Figure 6:
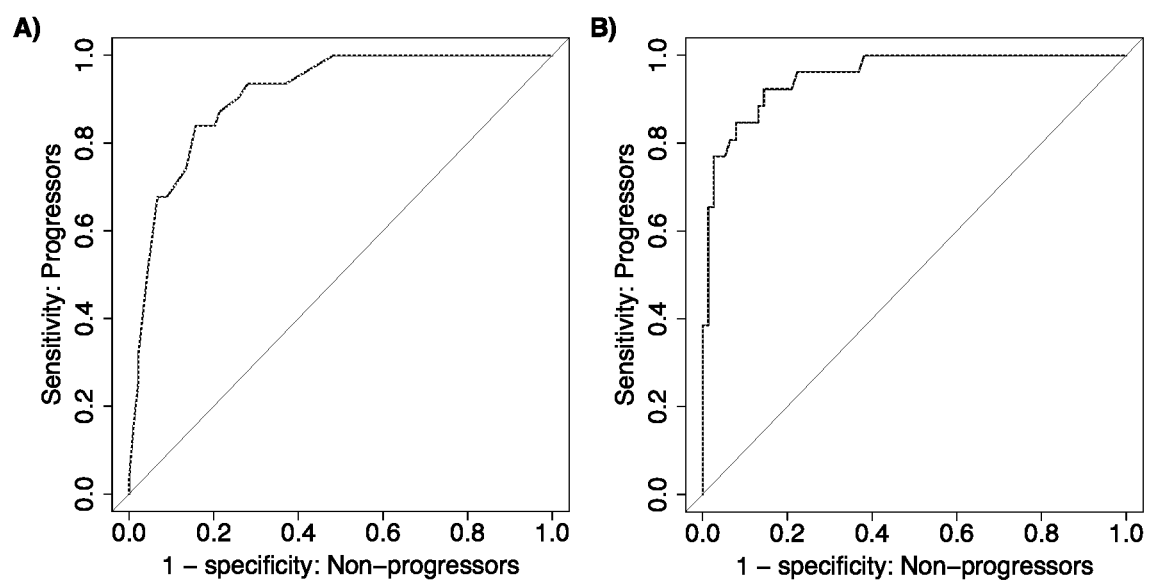
FIG. 6: Translation of RNA-seq signatures to qRT-PCR. A. Receiver operating characteristic curve for the South Africa qRT-PCR signature fit to the South Africa training set. AUC [95% CI]=0.91 [0.86-0.96]. B. Receiver operating characteristic curve for the Gambia qRT-PCR signature fit to the Gambia training set. AUC [95% CI]=0.95 [0.92-0.99].

A Four-Gene Correlate of Risk Signature Predicts TB Progression in Household Contacts South African and Gambian HHC cohorts were divided into training and test sets, while the entire Ethiopian cohort was assigned to the test set due to its small sample size. Samples from Uganda were not available in sufficient quantities for this analysis (FIG. 1). The South African and Gambian training sets were utilised to construct site-specific signatures of TB risk, using RNA-seq transcriptomes and the Pair Ratio approach, which uses ratios of transcripts that were regulated in opposite directions during TB progression, as a means to magnify TB-associated signals and simultaneously standardize for RNA concentration by focusing on regulation in opposite directions. Leave-one-out cross-validation analysis (LOOCV; applied to all samples from specific individuals) indicated strong potential for predicting TB progression in both cohorts (South Africa: FIG. 2A; area under the receiver operating characteristic curve (AUC)= 0.86 [95% CI: 0.79-0.94], $p=8.4 \times 10^{-10}$; The Gambia: FIG. 2B; AUC=0.77 [0.66-0.88]; $p=2.5 \times 10^{-10}$). Applying the algorithm to the South African and Gambian cohorts generated two distinct risk signatures (FIGS. 2C and D). When measured by qRT-PCR using primer/probe sets that corresponded to the exons, predictive accuracy was maintained (FIG. 6). Surprisingly, the two signatures were not strongly cross-predictive when applied to samples from the other country (FIGS. 2A and B). The South Africa signature weakly validated on Gambian samples (FIG. 2B; AUC=0.66 [0.54-0.76], $p=8.8 \times 10^{-3}$), while The Gambia signature failed to validate on samples from South Africa (FIG. 2A; AUC=0.59 [0.46-0.73], p=0.061), suggesting site-specific progression signatures in South Africa and The Gambia.

The poor cross-prediction of the South Africa and The Gambia signatures motivated explicit development of a multi-cohort signature using a training set that combined samples from both sites. The PCR-based transcript pairs that comprised all the South Africa (38 transcripts) and The Gambia (35 transcripts) signatures (FIGS. 2C and D) were pooled and transcript pairs that were significantly predictive of TB progression in both cohorts were identified. This analysis on RT-PCR data was also carried out using the "Pair Ratios" framework[3]. A single pair of transcripts that best fitted the entire training set was first identified, and then the next best pair was successively added to the ensemble, and the predictive power was re-assessed at each stage. This procedure was carried out until addition of pairs led to no further increase in predictive power. This resulted in a signature comprising two transcript pairs constructed from four unique genes: GAS6 and SEPT4 were up-regulated, whereas CD1C and BLK were down-regulated in progressors vs. matched controls (FIG. 3A). This signature is referred to herein as "RISK4".

The multi-site PCR-based signature of risk was validated by blind prediction of TB progression on the multi-cohort test sets from South Africa, The Gambia and Ethiopia (FIG. 1). The RISK4 signature successfully predicted progression in the entire combined test set (AUC=0.67 [0.57-0.77], $p=2.6 \times 10^{-4}$, FIG. 3B), and on each individual site (South Africa, The Gambia, and Ethiopia with AUCs: 0.66-0.72, p<0.03, FIG. 3B). Surprisingly, performance of the signature on combined test set samples within a year of TB diagnosis (AUC=0.66 [0.55-0.78], $p=1.9 \times 10^{-3}$, FIG. 3C) was comparable to samples collected more than a year before diagnosis (AUCs=0.69 [0.51-0.86], p=0.015). Deployment of such a risk signature in a screen-and-treat strategy in TB HHC would most likely entail testing early after exposure. Therefore, the predictive performance of RISK4 on samples from HHC collected within two months of diagnosis of the index case was assesses, and indeed it also validated in this setting (FIG. 3D; AUC=0.69 [0.52-0.86], $p=4.8 \times 10^{-3}$). Finally, to further corroborate the robustness of RISK4, blinded predictions were performed on samples from an external cohort of IGRA+/TST+ South African adolescents (the "ACS" cohort), where the time of TB exposure was unknown[1].

RISK4 also significantly predicted risk of TB progression in this cohort (FIG. 3E; AUC=0.69 [0.62-0.76], $p=3.4 \times 10^{-7}$).

Comparison of RISK4 with Published Diagnostic TB Signatures

To benchmark the predictive performance of the RISK4 signature, it was compared to qRT-PCR-based versions of three published transcriptional signatures for TB diagnosis: "DIAG3" (the 3-gene diagnostic signature by Sweeney et al[5]), "DIAG4" (the 4-gene diagnostic signature by Maertzdorf et al[4]), and a previously-reported 16-gene COR signature for TB progression ("ACS COR", Zak et al[1]). The three signatures predicted TB progression in the combined test set with comparable accuracy to RISK4 (FIG. 4A, AUCs of 0.64-0.68, $p<3 \times 10^{-3}$). However, unlike RISK4 (FIG. 3B), the three other signatures did not validate on all sites when evaluated individually (FIGS. 4B-D), suggesting that RISK4 represents a more generally applicable prognostic signature.

After unblinding the South African, Gambian, and Ethiopian test sets, interrogations were conducted to determine whether the RISK4 signature could be reduced to a single pair of transcripts without a loss of predictive accuracy. Each of the four ratios in the RISK4 signature was applied to each of the test set cohorts individually, and the performance thereof was compared to the entire RISK4 signature (Table 8). The ratio between the SEPT4 and BLK primers reproduced the performance of the RISK4 signature on all three test set cohorts, demonstrating feasibility of a highly simplified, 2-gene host RNA-based signature for identifying HHC at greatest risk of progressing to active TB.

TABLE 8

Performance of individual transcript pairs compared to the full GC64 signature (AUC values)

|  | SUN Test | MRC Test | AHRI Test | All Test |
| --- | --- | --- | --- | --- |
| RISK4 | 0.72 | 0.72 | 0.67 | 0.67 |
| SEPT4/BLK | 0.72 | 0.74 | 0.65 | 0.68 |
| SEPT4/CD1C | 0.77 | 0.68 | 0.59 | 0.63 |
| GAS6/BLK | 0.64 | 0.72 | 0.78 | 0.70 |
| GAS6/CD1C | 0.68 | 0.64 | 0.65 | 0.61 |

Meta-Analysis Identifies Gene Pairs that Predict TB Progression Across Africa

Figure 3:
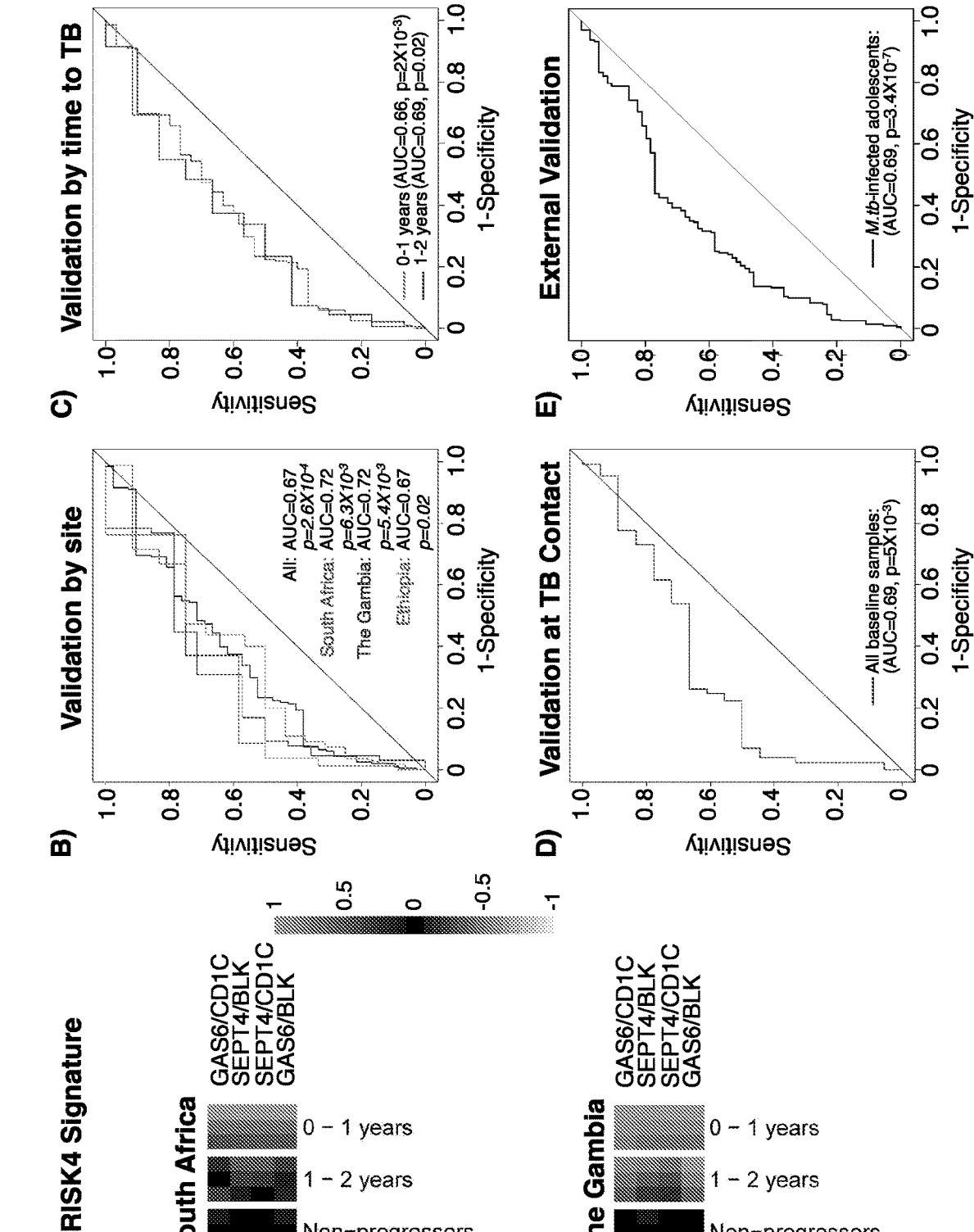
FIG. 3: Validation of a multi-cohort 4-gene (RISK4) signature derived from the South African and Gambia training sets. (A) Expression ratio of gene pairs in the RISK4 signature, in South Africa (top) and The Gambia (bottom) training set: non-progressors (left columns), progressors 1-2 years before diagnosis (middle columns), and progressors 0-1 (right columns) years before diagnosis. In each group, the central column is the mean fold expression over non-progressors, while left/right columns in each group correspond to mean−/+ standard error of the mean. (B) ROC curves for blind predictions of RISK4 on test set samples of all sites (black: AUC=0.67 [0.57-0.77], p=$2.6 \times 10^{-4}$), South Africa (red: AUC=0.72 [0.53-0.92], p=$6.3 \times 10^{-3}$), The Gambia (blue: AUC=0.72 [0.55-0.88], p=$5.4 \times 10^{-3}$), and Ethiopia (green: AUC=0.67 [0.5-0.83], p=0.02). (C) Performance of RISK4 signature in test set samples taken within one year of diagnosis (red; AUC=0.66 [0.55-0.78], p=$1.9 \times 10^{-3}$; 30 progressor samples, 201 non-progressor samples) or 1-2 years before diagnosis (blue; AUC=0.69 [0.51-0.86], p=0.015; 12 progressor samples, 201 non-progressor samples). (D) ROC curve of RISK4 on all baseline test set samples (AUC=0.69 [0.52-0.86], p=$4.8 \times 10^{-3}$). (E) ROC curve blind prediction of RISK4 in latently M.tb-infected South African adolescents (AUC=0.69 [0.62-0.76], p=$3.4 \times 10^{-7}$).

Overall, predictions for TB progression were the least accurate for the Ethiopian cohort, which was not used to develop the initial RISK4 signature (FIGS. 1, 3 and 4). To determine whether further improved accuracy could be achieved for a signature performing well at all sites, a meta-analysis of RNA-seq profiles was performed for the combined training and test datasets from all three cohorts. This analysis was focused on identifying better predictive gene pairs, given that the single transcript pair SEPT4/BLK performed equivalently to the RISK4 signature (Table 8).

RNA-seq data from all training and test cohorts was combined, thus merging the three independent cohorts from South Africa, The Gambia and Ethiopia. Pairs of up-regulated and down-regulated transcripts were formed from all transcripts that individually discriminated progressors from controls in at least one cohort (Wilcoxon FDR<0.05 in at least one of the three cohorts). Each pair was then analyzed on each of the three sites. Nine transcript pairs that discriminated progressors from controls with AUC>0.75 on all three sites were identified (Table 9). The optimal pair consisted of C1QC (up-regulated) and TRAV27 (down-regulated) and achieved AUC>0.76 on all three sites. Logistic regression analysis was performed to determine whether the remaining eight pairs (Table 10) captured information about TB progression that was redundant or complementary to the signals detected by C1QC/TRAV27. The ratio between ANKRD22 (up-regulated with TB progression) and OSBPL10 (down-regulated with progression) led to significantly increased discrimination between progressors and controls when it was combined with the C1QC/TRAV27 ratio in HHC cohorts (FIGS. 5A-C, 7), increasing the ROC AUC on all three HHC cohorts individually to AUC>0.79 (Table 11). Thus, the ratios C1QC/TRAV27 and ANKRD22/OSBPL10 capture distinct aspects of TB progression signals in HHC that are shared across three distinct African sites.

TABLE 9

Transcript pairs that discriminate progressors from controls

C1QC/TRAV27
C1QA/TBCB
C1QC/RP3-395M20.9
C1QC/PIK3C2B
C1QC/RPIA
C1QC/NELL2
C1QC/OSBPL10
ANKRD22/OSBPL10
RHBDF2/TUBGCP6

TABLE 10

The ability of all pairs with AUC > 0.75 in all three cohorts to complement the top pair (C1QC/TRAV27) was analyzed using logistic regression

|  | C1QA/ TBCB | C1QC/RP3- 395M20.9 | C1QC/ PIK3C2B | C1QC/ RPIA | C1QC/ NELL2 | C1QC/ OSBPL10 | ANKRD22/ OSBPL10 | RHBDF2/ TUBGCP6 |
|---|---|---|---|---|---|---|---|---|
| SUN | 0.002 | 0.108 | 0.178 | 0.635 | 0.271 | 0.099 | 0.0004 | 0.035 |
| MRC | 0.245 | 0.011 | 0.594 | 0.807 | 0.806 | 0.143 | 0.006 | 0.027 |
| AHRI | 0.126 | 0.157 | 0.123 | 0.305 | 0.084 | 0.047 | 0.032 | 0.167 |

TABLE 11

AUCs of C1QC/TRAV27, ANKRD22/OBSPL10 and the combination of the two on all three cohorts

|  | AUC | | |
|---|---|---|---|
|  | SUN | MRC | AHRI |
| C1QC/TRAV27 | 0.761 | 0.771 | 0.769 |
| ANKRD22/OBSPL10 | 0.757 | 0.754 | 0.777 |
| C1QC/TRAV27 + ANKRD22/OBSPL10 | 0.801 | 0.796 | 0.795 |

Figure 5:
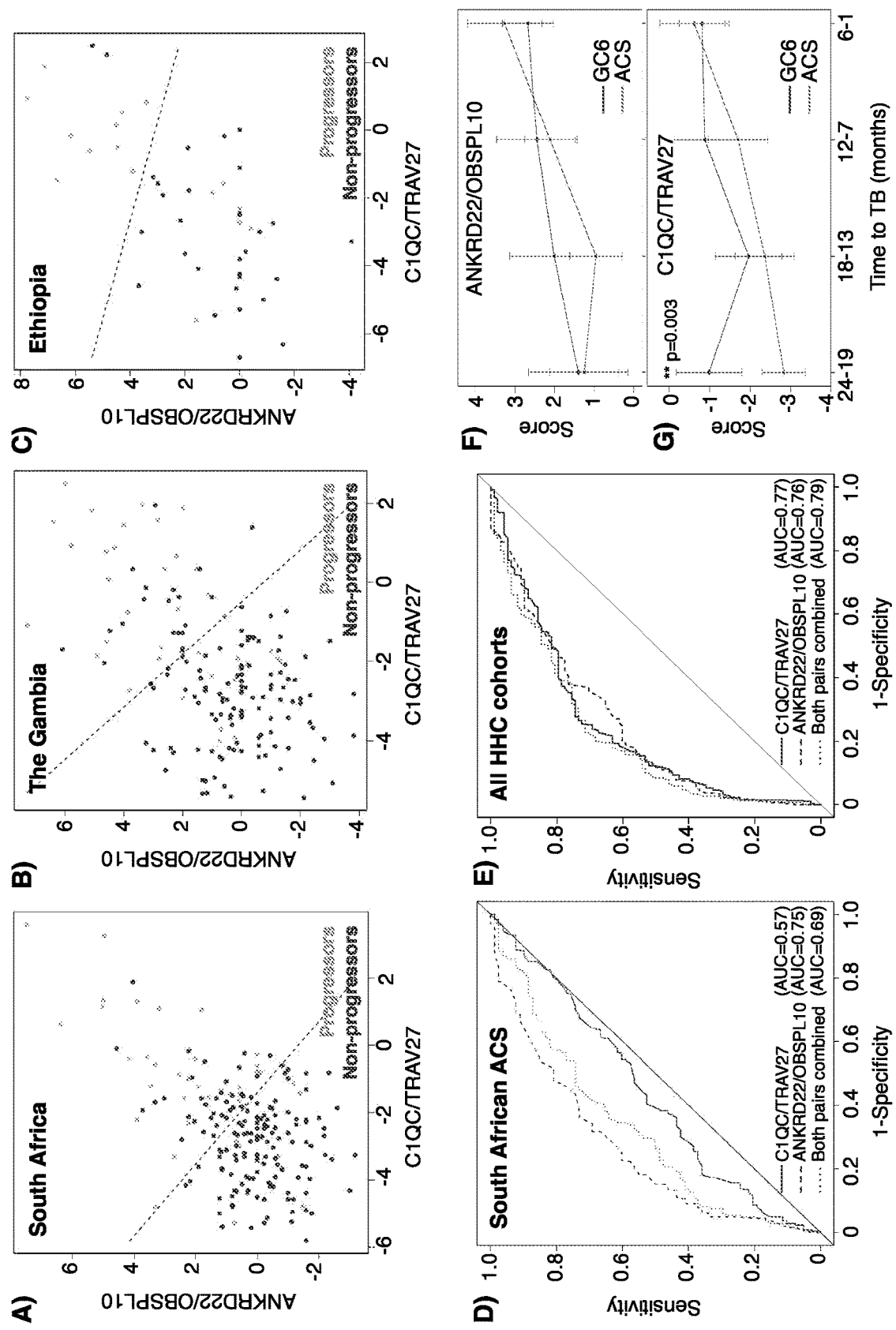
FIG. 5: Gene pairs to predict TB progression in African cohorts. Ratios of C1QC/TRAV27 and ANKRD22/OBSPL10 plotted on samples from South Africa (A), The Gambia (B), and Ethiopia (C) along with an optimal discriminant (dashed line; optimizes sum of sensitivity and specificity) separating progressors (orange) from non-progressors (blue). On each cohort, the two pairs provide complementary information; p-values correspond to Chi-square complementation analysis in Table 10. (D) ROC curves showing the ability of the GC6-trained C1QC/TRAV27 (solid; AUC=0.57 [0.49-0.64], p=0.042), ANKRD22/OBSPL10 (dashed; AUC=0.75 [0.68-0.81], p=$2.86 \times 10^{-11}$), and a linear combination of C1QC/TRAV27 and ANKRD22/OBSPL10 (dotted; AUC=0.69 [0.61-0.76], p=$4.3 \times 10^{-07}$) models to predict TB disease progression on in the ACS cohort. (F and G) Log-ratios of expression (mean+/−95% confidence interval) for ANKRD22/OBSPL10 (F) and C1QC/TRAV27 (G) are plotted as a function of time to diagnosis, for both GC6 (blue) and ACS (red) progressor samples. Comparison of C1QC/TRAV27 expression at 19-24 months before diagnosis, between the GC6-74 HHC and ACS cohorts was statistically significantly different (p=$3 \times 10^{-3}$) using the Mann-Whitney U test.

To determine whether the C1QC/TRAV27 and ANKRD22/OSBPL10 signatures captured universal aspects of TB progression rather than HHC-associated biology, they were evaluated using data from the cohort of IGRA+TST+ South African adolescents[1]. The ANKRD22/OBSPL10 ratio strongly predicted TB progression among the M.tb-infected adolescents (FIG. 5D; AUC=0.75 [0.68-0.81], p=2.86× $10^{-11}$), but the C1QC/TRAV27 ratio was poorly predictive in the adolescent cohort (FIG. 5D; AUC=0.57 [0.49-0.64], p=0.042). In contrast to the HHC, combining the two ratios did not lead to improved discrimination of progressors and controls in the adolescent cohort (AUC=0.69 [0.61-0.76]; FIG. 5D). To further understand the disparity in the predictive performance for the HHC cohorts and the M.tb-infected adolescents, the longitudinal behavior of the transcript ratios for progressor samples in the HHC and adolescent cohorts was evaluated (FIGS. 5F and 5G). The ANKRD22/OSBPL10 pair exhibited similar behavior in the HHC and ACS, with a steady up-regulation during progression and no significant difference between GC6-74 and adolescent participants in any 6-month time window preceding TB diagnosis (FIG. 5F). In contrast, the C1QC/TRAV27 ratio was significantly higher in HHC progressors than in M.tb-infected adolescents 19-24 months before TB diagnosis (p=3× $10^{-3}$, FIG. 5G). Importantly, samples from HHC progressors were collected mostly at enrolment, immediately following exposure to the respective TB index cases, thus possibly representing a signature of M.tb exposure.

Example 1—Patient Likely to Transition to Active TB Based on RISK4 (Positive)

A blood sample was obtained from a patient, and RNA was extracted using an RNA extraction kit and cDNA generated using a standard RT-PCR reaction. Gene expression levels of SEPT4, GAS6, CD1C and BLK were determined by the method of microfluidic, quantitative real-time PCR using TaqMan primer/probe sets on the BioMark (Fluidigm). The expression level of SEPT4 was 13.69727798 Ct; the expression level of GAS6 was 12.29700099 Ct; the expression level of CD1C was 14.01581047 Ct; and the expression level of BLK was 12.17445854 Ct.

The ratios of expression were calculated as gene 2 Ct-gene 1 Ct, and these were then looked-up in the relevant lookup table (Tables 2 to 5), and matched with the first value in column 1 which is just greater (or equal to) the pair ratio. The value in column 2 of the lookup table was assigned as the score for the relevant pair, and the RISK4 score was calculated as an average of the lookup table pair scores.

The ratio of expression for SEPT4:CD1C was calculated and this was 0.31853249. Using Table 4, a score of 0.8386821 was assigned to this ratio of expression. The ratio of expression for GAS6:CD1C was calculated and this was 1.71880948. Using Table 2, a score of 0.9912281 was assigned to this ratio of expression. The ratio of expression for SEPT4:BLK was calculated and this was −1.52281944. Using Table 3, a score of 0.7410676 was assigned to this ratio of expression. The ratio of expression for GAS6:BLK was calculated and this was −0.12254245. Using Table 5, a score of 0.9824561 was assigned to this ratio of expression. The RISK4 score was calculated as the average of the four gene pair scores from the lookup tables and this was 0.888358475 (Table 12).

TABLE 12

Calculation of RISK4 score for patient 1

| Gene1 | Gene2 | Ratio (Gene 2-Gene1) | Lookup Table Score |
|---|---|---|---|
| GAS6 | CD1C | 1.71880948 | 0.9912281 |
| SEPT4 | BLK | −1.52281944 | 0.7410676) |
| SEPT4 | CD1C | 0.31853249 | 0.8386821 |

TABLE 12-continued

Calculation of RISK4 score for patient 1

| Gene1 | Gene2 | Ratio (Gene 2-Gene1) | Lookup Table Score |
|---|---|---|---|
| GAS6 | BLK | −0.12254245 | 0.9824561 |
| | | | Average (RISK4 score) = 0.888358475 |

For the conditions of this example, a score of 0.4 had previously been selected as being the cut-off for patients who are likely to transition to TB. As the patient's score was above 0.4, the patient was identified as being likely to transition to active TB.

Example 2—Patient Unlikely to Transition to Active TB Based on RISK4 (Negative)

A blood sample was obtained from a patient, RNA was extracted, cDNA was generated and gene expression levels of SEPT4, GAS6, CD1C and BLK were determined as described in the previous example. The expression level of SEPT4 was 17.54688044 Ct; the expression level of GAS6 was 17.86573837 Ct, the expression level of CD1C was 15.17873605 Ct; and the expression level of BLK was 13.96526762 Ct. The ratio of expression for SEPT4:CD1C was calculated and this was −2.36814439. Using Table 4, a score of 0.1242512 was assigned to this ratio of expression. The ratio of expression for GAS6:CD1C was calculated and this was −2.68700232. Using Table 2, a score of 0.04210526 was assigned to this ratio of expression. The ratio of expression for SEPT4:BLK was calculated and this was −3.58161282. Using Table 3, a score of 0.1726573 was assigned to this ratio of expression. The ratio of expression for GAS6:BLK was calculated and this was −3.90047075. Using Table 5, a score of 0.07783094 was assigned to this ratio of expression. The RISK4 score was calculated as the average of the four gene pair scores from the lookup tables and this was 0.104211175 (Table 13).

TABLE 13

Calculation of RISK4 score for patient 2

| Gene1 | Gene2 | Ratio (Gene 2-Gene1) | Lookup Table Score |
|---|---|---|---|
| GAS6 | CD1C | −2.68700232 | 0.04210526 |
| SEPT4 | BLK | −3.58161282 | 0.1726573 |
| SEPT4 | CD1C | −2.36814439 | 0.1242512 |
| GAS6 | BLK | −3.90047075 | 0.07783094 |
| | | | Average (RISK4 score) = 0.104211175 |

For the conditions of this example, a score of 0.4 had previously been selected as being the cut-off for patients who are likely to transition to TB. As the present score was below 0.4, the patient was identified as being likely to transition to active TB.

Discussion

A simple, easily implementable, PCR-based transcriptomic signature was identified ("RISK4"), to predict risk of progression to active TB disease in diverse African cohorts of recently exposed HHC of index TB cases. This four-gene signature predicted risk of progression with similar accuracy in 4 cohorts from 3 Sub-Saharan African populations with heterogeneous genetic backgrounds, TB epidemiology and circulating M.tb strains. Importantly, RISK4 exhibited consistent predictive performance in all test set cohorts, while previously reported signatures[1,4,5] exhibited cohort-specific variability in performance. It was previously reported that the ACS COR signature validated on the entire South African and Gambian HHC cohorts, which were not separated into training and test sets[1]. Failure of the ACS COR to predict TB progression on The Gambian test set, as reported here, is likely a function of the sample distribution in the small test set compared with the full Gambian HHC cohort[1].

The signatures reported herein represent significant and translational improvements over currently used biomarkers for predicting risk of TB, such as IGRAs or TST. Recent estimates suggest the TB incidence of South Africa and The Gambia to be 0.8% and 0.3%, respectively. However, IGRA and TST-positive prevalence can reach up to 50% in The Gambia and 80% in South Africa and although IGRA and TST have a high (approximately 80%) sensitivity for M.tb infection, they have poor positive predictive values (PPV) of 2.7% and 1.5%, respectively for TB progression. Therefore, dozens of individuals would require prophylactic treatment to prevent progression to TB in a single individual. The target product profile for a non-sputum based TB risk test states that it should be a rule-out test with high sensitivity, such that individuals at high risk of TB progression are unlikely to be falsely excluded and are referred for additional investigation for TB or offered prophylactic treatment. At sensitivities of 81, 71, 62 and 50% the RISK4 signature achieves specificities of 34, 52, 63 and 77% in healthy asymptomatic individuals, respectively, by selection of different thresholds (Table 12). Although RISK4 has a similar poor PPV of 3% to IGRA tests or the TST, it importantly has lower positivity rates in the target population. To achieve a test performance similar to IGRAs (between 70 to 80% sensitivity and the number to harm (NTH) to prevent one case of approximately 85), the RISK4 threshold would identify between 38 and 54% of household contacts for preventative measures, compared to 78% for IGRA (Table 14).

TABLE 14

Performance of RISK4 at different sensitivities

| RISK4 Threshold | Sensitivity | Specificity: all sites | Specificity: SUN, South Africa | Specificity: MRC, Gambia | Specificity: AHRI, Ethiopia | RISK4 Positivity Rate in nested cohort | TB Incidence in entire GC6 cohort (Control event rate (CER)) | RISK4 Threshold | Proportion of Incident cases detected by RISK4 | Proportion of incidents not detected (Experimental event rate-EER) | Potential absolute risk reduction (ARR) by RISK4-guided preventative treatment | Number to harm (NTH) (number ideintified for RISK4-guided prevention) |
|---|---|---|---|---|---|---|---|---|---|---|---|---|
| 0.05 | 100% | 1% | 1% | 22% | 24% | 98% | 0.022 | 0.05 | 0.02200 | 0.00000 | 0.02200 | 45 |
| 0.35 | 90% | 30% | 28% | 22% | 24% | 61% | 0.022 | 0.35 | 0.01990 | 0.00210 | 0.01990 | 50 |

TABLE 14-continued

Performance of RISK4 at different sensitivities

| RISK4 Threshold | Sensitivity | Specificity: all sites | Specificity: SUN, South Africa | Specificity: MRC, Gambia | Specificity: AHRI, Ethiopia | RISK4 Positivity Rate in nested cohort | TB Incidence in entire GC6 cohort (Control event rate (CER)) | RISK4 Threshold | Proportion of Incident cases detected by RISK4 | Proportion of incidents not detected (Experimental event rate-EER) | Potential absolute risk reduction (ARR) by RISK4-guided preventative treatment | Number to harm (NTH) (number ideintified for RISK4-guided prevention) |
|---|---|---|---|---|---|---|---|---|---|---|---|---|
| 0.37 | 81% | 34% | 33% | 23% | 24% | 54% | 0.022 | 0.37 | 0.01781 | 0.00419 | 0.01781 | 56 |
| 0.49 | 71% | 52% | 63% | 69% | 53% | 38% | 0.022 | 0.49 | 0.01571 | 0.00629 | 0.01571 | 64 |
| 0.57 | 62% | 63% | 63% | 69% | 56% | 29% | 0.022 | 0.57 | 0.01362 | 0.00838 | 0.01362 | 73 |
| 0.67 | 50% | 77% | 96% | 91% | 80% | 19% | 0.022 | 0.67 | 0.01100 | 0.01100 | 0.01100 | 91 |
| 0.73 | 40% | 81% | 96% | 92% | 89% | 17% | 0.022 | 0.73 | 0.00890 | 0.01310 | 0.00890 | 112 |
| 0.85 | 31% | 94% | 99% | 95% | 93% | 6% | 0.022 | 0.85 | 0.00681 | 0.01519 | 0.00681 | 147 |
| 0.92 | 21% | 98% | 99% | 95% | 96% | 2% | 0.022 | 0.92 | 0.00471 | 0.01729 | 0.00471 | 212 |
| 0.94 | 12% | 98% | 99% | 97% | 98% | 1% | 0.022 | 0.94 | 0.00262 | 0.01938 | 0.00262 | 382 |

Several transcript pairs were identified that recapitulated the predictive performance of the RISK4 signature and reflected complementary signals in predicting risk of TB progression. The most universal pair defined in this meta-analysis showed up-regulation of the complement C1q C-chain (C1QC), and down-regulation of T-cell receptor alpha variable gene 27 (TRAV27). Interestingly, complement pathway genes are markedly up-regulated following M.tb infection of non-human primates, consistent with the up-regulation of C1QC/TRAV27 at baseline in the HHC. Complement activation is also observed early during human progression to TB while C1q is down-regulated early after starting TB treatment, suggesting that C1q may be a proxy of early TB pathology. Conversely, down-regulation of TRAV27, and several other T-cell genes, is likely associated with the overall decrease in peripheral T-cell frequencies and their associated gene expression modules during TB progression, potentially due to migration of T-cells to the disease site. The simple C1QC/TRAV27 signal may thus be a read-out of TB risk following initial exposure to a pulmonary TB case, which is more synchronized in a HHC study design, even though prior exposure to M.tb cannot be ruled out in this study, and progression to TB disease within the first three months of the observation period were excluded from the analysis. This may explain why C1QC/TRAV27 signal was less predictive in the natural history cohort of M.tb-infected adolescents, where the time of M.tb exposure was unspecified. Early clinical studies suggest that recent exposure to M.tb, indicated by TST conversion, can correlate with symptoms consistent with febrile disease, such as fever and erythema nodosum, markers of systemic inflammation. C1QC/TRAV27 may reflect this inflammatory response induced by failed containment of M.tb following recent exposure.

Overall, a simple cost-effective PCR-based test from accessible blood samples that predicts TB in heterogeneous African populations with intermediate to high TB burdens[1] has been identified and validated. The test can be used to screen for risk of progression during TB contact investigation, implemented by national public health structures.

The four-transcript signature described above (designated "RISK4" by the applicants), derived from samples in a South African and Gambian training set, reflects subclinical disease prior to manifestation of active TB and predicted progression up to two years before onset of disease in blinded test set samples from South Africa, The Gambia and Ethiopia with little population-associated variability and also validated on an external cohort of South African adolescents with latent *Mycobacterium tuberculosis* infection. This signature surpassed published signatures in its ability to predict TB progression in different African cohorts. For example, published diagnostic or prognostic tuberculosis signatures predicted on samples from some, but not all 3 countries, indicating site-specific variability.

This simple 4-marker test, or even the 2-marker test of SEPT4/BLK, could be translated into a simple, rapid and affordable point-of-care test for field application in resource-limited settings where TB and M.tb infection are endemic to identify individuals at high risk of developing TB. Early detection of individuals at high risk of developing TB, or detection of subclinical TB in the absence of disease symptoms or available sputum for microbiological diagnosis, when disease pathology has not yet fully developed and the bacterial load is low to absent, could allow these individuals to be prioritized for prophylactic interventions. This timely intervention could prevent disease outbreak.

Identifying infected people at high risk of developing active TB will also facilitate targeted enrolment into drug trials and post-exposure vaccine trials, thus profoundly reducing number of study participants and trial duration.

The tests using these signatures are based on accessible samples, such as blood, and could yield rapid results as antigen stimulation is not required. Computing the score requires basic arithmetic and the pair-ratio structure eliminates the need for housekeepers or other standardization methods. Measurement of the transcript levels can therefore be easily translated to field-friendly PCR devices for simple qRT-PCR-based point-of-care tests.

The signatures of the present invention were developed based on samples of subjects who had been exposed to an index (active) TB patient living in the same household. These subjects, referred to as household contacts (HHC), constitute an important target population for preventative measures as they are at high risk of infection with *Mycobacterium tuberculosis* and progression to disease. However, it will be apparent that the signatures of the present invention can be used to identify individuals who are at risk of developing active TB, even if it is not known if they have had contact with an active TB patient or if the TB patient does not live within their household. For example, other risk factors include HIV infection, poverty, geographic location, chronic lung disease, poverty, diabetes, genetic susceptibility, imprisonment, etc.

REFERENCES

1. Zak, D. E., et al. A blood RNA signature for tuberculosis disease risk: a prospective cohort study. *Lancet* 387, 2312-2322 (2016).
2. Mahomed, H., et al. Predictive factors for latent tuberculosis infection among adolescents in a high-burden area in South Africa. *Int J Tuberc Lung Dis* 15, 331-336 (2011).
3. Thompson, E. G., et al. Host blood RNA signatures predict the outcome of tuberculosis treatment. *Tuberculosis* 107, 48-58 (2017).
4. Maertzdorf, J., et al. Concise gene signature for point-of-care classification of tuberculosis. *EMBO Mol Med* 8, 86-95 (2016).
5. Sweeney, T. E., Braviak, L., Tato, C. M. & Khatri, P. Genome-wide expression for diagnosis of pulmonary tuberculosis: a multicohort analysis. *Lancet Respir Med* 4, 213-224 (2016).

The invention claimed is:

1. A method for diagnosing a human subject as likely to develop active tuberculosis (TB) disease and treating the subject, the method comprising:

a) detecting mRNA expression levels of SEPT4, BLK, GAS6 and CD1C, in a blood sample from the human subject;

b) calculating the ratio of the expression levels for SEPT4:BLK, SEPT4:CD1C, GAS6:BLK and GAS6:CD1C, assigning a score to each expression ratio, and calculating the average of the assigned scores;

c) comparing the average of the assigned scores to a threshold value, wherein the average of the assigned scores is above the threshold value and the subject is identified as being likely to develop active TB; and d) administering treatment for tuberculosis infection to the subject.

2. The method according to claim 1, wherein the treatment is prophylactic treatment.

3. The method according to claim 1, wherein the score is an indication of whether the subject is likely to transition to active TB disease within a period of 2 years.

* * * * *

UNITED STATES PATENT AND TRADEMARK OFFICE
CERTIFICATE OF CORRECTION

PATENT NO. : 11,613,782 B2
APPLICATION NO. : 16/980121
DATED : March 28, 2023
INVENTOR(S) : Suliman et al.

Page 1 of 2

It is certified that error appears in the above-identified patent and that said Letters Patent is hereby corrected as shown below:

On the Title Page

(71) Applicants: Please correct "SEATTLE CHILDREN'S HOSPITAL, Seattle, WA (US);" to read --SEATTLE CHILDREN'S HOSPITAL DOING BUSINESS AS SEATTLE CHILDREN'S RESEARCH INSTITUTE, Seattle, WA (US);--

(73) Assignees: Please correct "SEATTLE CHILDREN'S HOSPITAL, Seattle, WA (US);" to read --SEATTLE CHILDREN'S HOSPITAL DOING BUSINESS AS SEATTLE CHILDREN'S RESEARCH INSTITUTE, Seattle, WA (US);--

In the Specification

Column 5, Line 2: Please correct "mean-/+" to read --mean -/+--

Column 5, Line 15: Please correct "mean-/+" to read --mean -/+--

Column 5, Line 63: Please correct "(mean-/+95%" to read --(mean -/+ 95%--

Column 25, Line 25: Please correct "numberwere" to read --number ≥7 were--

Signed and Sealed this
Twenty-seventh Day of August, 2024

Katherine Kelly Vidal
*Director of the United States Patent and Trademark Office*

Columns 31-34, Table 14: Please delete Table 14 and replace with the following:

Table 14: Performance of RISK4 at different sensitivities

| RISK4 Threshold | Sensitivity | Specificity: all sites | Specificity: SUN, South Africa | Specificity: MRC, Gambia | Specificity: AHRI, Ethiopia | RISK4 Positivity Rate in nested cohort | TB Incidence in entire GC6 cohort (Control event rate (CER)) | Proportion of Incident cases detected by RISK4 | Proportion of incidents not detected (Experimental event rate- EER) | Potential absolute risk reduction (ARR) by RISK4-guided preventative treatment | Number to harm (NTH) (number identified for RISK4-guided prevention) |
|---|---|---|---|---|---|---|---|---|---|---|---|
| 0.05 | 100% | 1% | 1% | 22% | 24% | 98% | 0.022 | 0.02200 | 0.00000 | 0.02200 | 45 |
| 0.35 | 90% | 30% | 28% | 22% | 24% | 61% | 0.022 | 0.01990 | 0.00210 | 0.01990 | 50 |
| 0.37 | 81% | 34% | 33% | 23% | 24% | 54% | 0.022 | 0.01781 | 0.00419 | 0.01781 | 56 |
| 0.49 | 71% | 52% | 63% | 69% | 53% | 38% | 0.022 | 0.01571 | 0.00629 | 0.01571 | 64 |
| 0.57 | 62% | 63% | 63% | 69% | 56% | 29% | 0.022 | 0.01362 | 0.00838 | 0.01362 | 73 |
| 0.67 | 50% | 77% | 95% | 91% | 80% | 19% | 0.022 | 0.01100 | 0.01100 | 0.01100 | 91 |
| 0.73 | 40% | 81% | 95% | 92% | 89% | 17% | 0.022 | 0.00890 | 0.01310 | 0.00890 | 112 |
| 0.85 | 31% | 94% | 99% | 95% | 93% | 6% | 0.022 | 0.00681 | 0.01519 | 0.00681 | 147 |
| 0.92 | 21% | 98% | 99% | 95% | 96% | 2% | 0.022 | 0.00471 | 0.01729 | 0.00471 | 212 |
| 0.94 | 12% | 98% | 99% | 97% | 98% | 1% | 0.022 | 0.00262 | 0.01938 | 0.00262 | 382 |